United States Patent
Britva et al.

(10) Patent No.: US 8,579,835 B2
(45) Date of Patent: Nov. 12, 2013

(54) APPARATUS AND METHOD FOR SELECTIVE ULTRASONIC DAMAGE OF ADIPOCYTES

(75) Inventors: Alexander Britva, Migdal Ha'emek (IL); Alexander Dverin, Netanya (IL); Ziv Karni, Kfar Shmaryahu (IL)

(73) Assignee: Alma Lasers Ltd., Caesarea (IL)

( * ) Notice: Subject to any disclaimer, the term of this patent is extended or adjusted under 35 U.S.C. 154(b) by 31 days.

(21) Appl. No.: 12/672,855

(22) PCT Filed: Feb. 1, 2009

(86) PCT No.: PCT/IB2009/050391
§ 371 (c)(1),
(2), (4) Date: Apr. 15, 2010

(87) PCT Pub. No.: WO2009/095894
PCT Pub. Date: Aug. 6, 2009

(65) Prior Publication Data
US 2011/0213279 A1     Sep. 1, 2011

Related U.S. Application Data

(60) Provisional application No. 61/063,355, filed on Feb. 1, 2008, provisional application No. 61/100,737, filed on Sep. 28, 2008.

(51) Int. Cl.
*A61H 1/00* (2006.01)
(52) U.S. Cl.
USPC .......................................................... 601/2
(58) Field of Classification Search
USPC .......................................................... 601/2
See application file for complete search history.

(56) References Cited

U.S. PATENT DOCUMENTS

| 5,460,595 A | 10/1995 | Hall et al. |
| 5,527,273 A | 6/1996 | Manna et al. |
| 5,549,544 A | 8/1996 | Young et al. |
| 6,450,979 B1 * | 9/2002 | Miwa et al. ..................... 601/2 |
| 7,331,951 B2 | 2/2008 | Eshel et al. |

(Continued)

FOREIGN PATENT DOCUMENTS

| DE | 10207813 | * | 4/2003 |
| FR | 2906165 | * | 3/2008 |

(Continued)

OTHER PUBLICATIONS

EPO office action for EP2252369 (parallel case in Europe), Rijswijk Netherlands, Jul. 22, 2011.

(Continued)

*Primary Examiner* — Tse Chen
*Assistant Examiner* — Hien Nguyen
(74) *Attorney, Agent, or Firm* — Marc Van Dyke

(57) ABSTRACT

An apparatus and a method for treating adipose tissue located beneath a patient's skin is disclosed herein. In some embodiments, the apparatus includes a sonotrode and an ultrasound transducer operative to induce longitudinal and/or transversal ultrasound vibrations in a least a portion of the sonotrode. In some embodiments, the apparatus provides a "cold" or "transverse" mode where ultrasound energy delivered to the patient is primarily energy of transverse ultrasound waves, and a "hot" or "longitudinal" mode where ultrasound energy delivered to the patient is primarily energy of longitudinal ultrasound waves. The longitudinal waves may be useful for 'pre-heating' tissue of the patient before delivering the transverse waves.

26 Claims, 19 Drawing Sheets

(56) References Cited

U.S. PATENT DOCUMENTS

| | | | |
|---|---|---|---|
| 7,431,704 B2 | 10/2008 | Babaev | |
| 2002/0077550 A1 | 6/2002 | Rabiner et al. | |
| 2006/0094988 A1* | 5/2006 | Tosaya et al. | 601/2 |
| 2006/0241531 A1 | 10/2006 | Gruber et al. | |
| 2007/0055154 A1 | 3/2007 | Torbati | |
| 2007/0232963 A1 | 10/2007 | Talish et al. | |
| 2008/0009885 A1 | 1/2008 | Del Giglio | |
| 2008/0058682 A1 | 3/2008 | Azhari et al. | |
| 2010/0010395 A1* | 1/2010 | Gagnepain et al. | 601/2 |

FOREIGN PATENT DOCUMENTS

| | | |
|---|---|---|
| JP | S63 305863 A | 12/1988 |
| JP | H03-054659 U | 5/1991 |
| JP | 10263038 | 10/1998 |
| JP | 2000116794 | 4/2000 |
| WO | WO9209238 | 6/1992 |
| WO | WO9316652 | 9/1993 |
| WO | WO0036981 | 6/2000 |

OTHER PUBLICATIONS

Response to Jul. 22, 2011 action for EP2252369, York, United Kingdom, Sep. 16, 2011.

Parallel JP application: summary of office communication received Aug. 18, 2011.

Machine Language translation of the abstract of JP10263038 Publication date Oct. 6, 1998.

PCT Search report of PCT/IB20091050391 (parent case) mailed Nov. 4, 2009.

PCT Search opinion of PCT/IB2009/050391 (parent case) Nov 4, 2009.

PCT Preliminary patentability opinion of PCT/IB2009/050391 (parent case) Apr. 30, 2010.

Office action for IL 207343 (parallel case in Israel; national phase entry of PCT/IB2009/050391—Office Action issued by the Israel Patent Office (Jerusalem, Israel) on Jun. 11, 2013.

* cited by examiner

Before Ultrasound Cell Rupturing

After Ultrasound Cell Rupturing

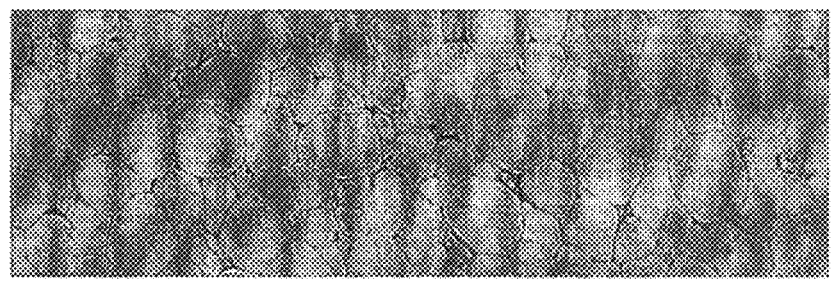
FIG. 5A  Before Ultrasound Damage
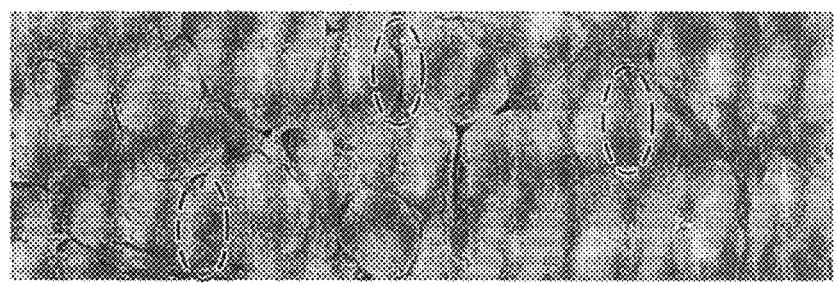
FIG. 5B  Immediately After Ultrasound Damage
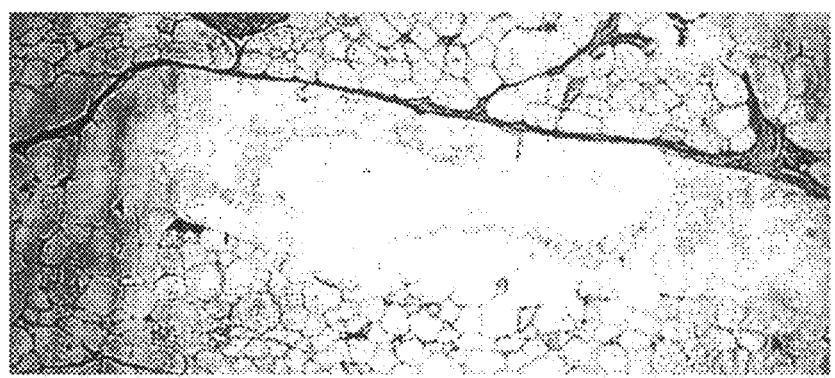
FIG. 5C  Three Days After Ultrasound Damage
FIG. 5D  Intact nerve and blood vessels surrounded by damaged fat tissue Example of implementation of step S511

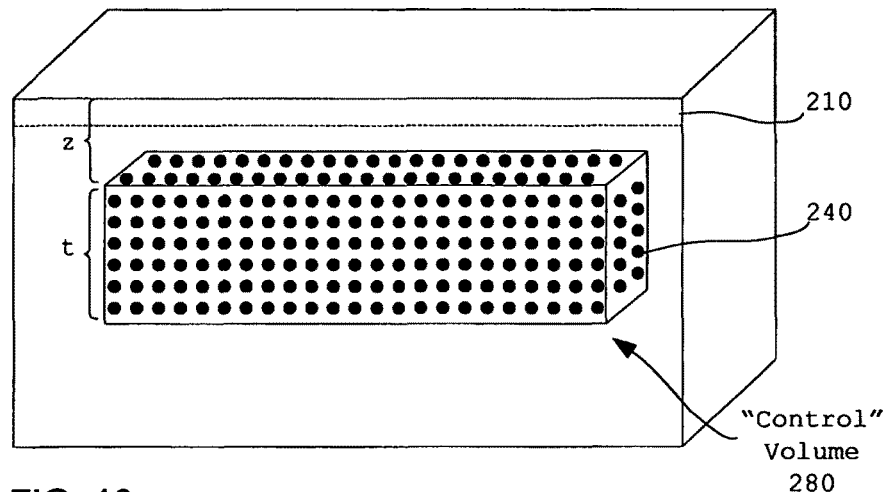
FIG. 10
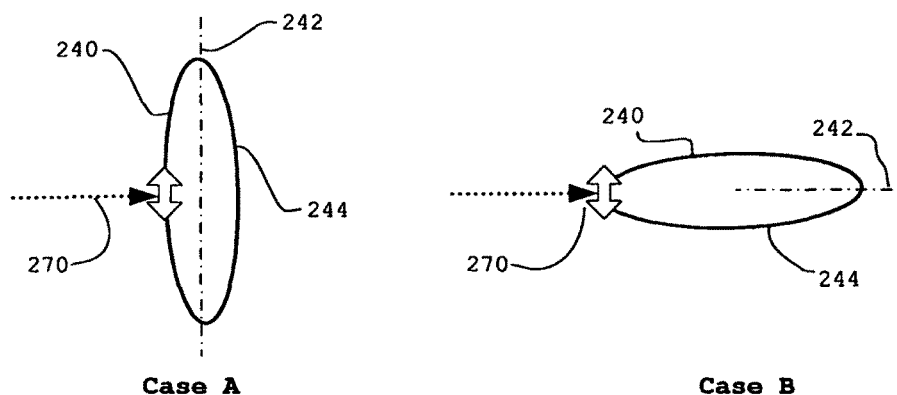
FIG. 11A
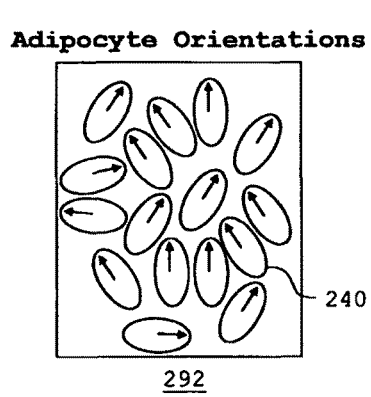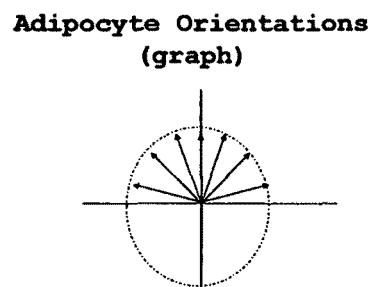
FIG. 11B

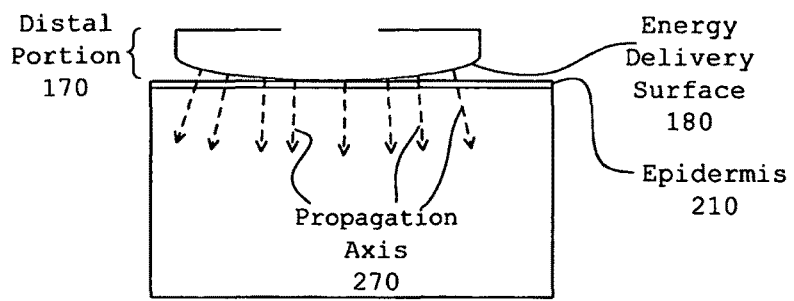
FIG. 12
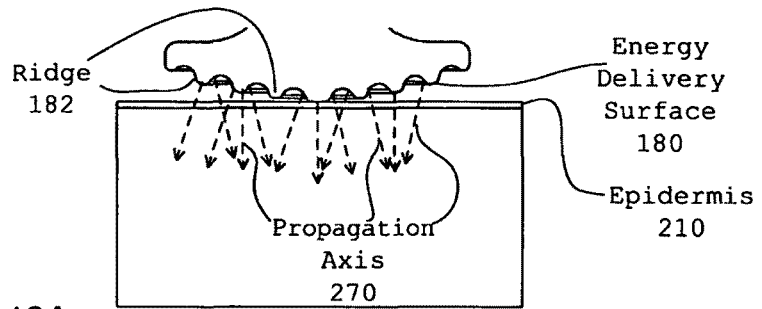
FIG. 13A
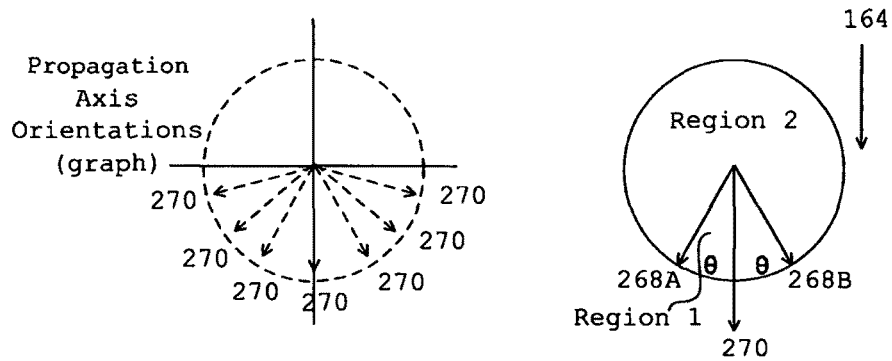
FIG. 13B  FIG. 13C

APPARATUS AND METHOD FOR SELECTIVE ULTRASONIC DAMAGE OF ADIPOCYTES

CROSS-REFERENCE TO RELATED APPLICATIONS

This patent application is a National Stage application filed under 35 U.S.C. §371 of PCT/IB2009/050391 filed on Feb. 1, 2009 and published as WO/2009/095894, which claims priority to U.S. Application 61/063,355 filed on Feb. 1, 2008 and to U.S. Application 61/100,737 filed on Sep. 28, 2008 which are all hereby incorporated in their entirety by reference.

FIELD OF THE INVENTION

The present invention relates to a method and an apparatus for treating adipose tissue with mechanical waves having an ultrasound frequency.

BACKGROUND AND RELATED ART

Techniques for instantly rupturing adipocytes using "longitudinal" or compressional ultrasound waves are known in the art. When ultrasound waves (for example, focused ultrasound waves) are applied to adipose tissue beneath the dermis, the ultrasound waves rupture the adipocytes in the adipose tissue, causing necrosis. This technique is "non-selective" and causes extensive collateral damage to other "proximate" tissues (i.e. blood vessels, connective tissue, dermis, epidermis etc).

FIG. 1A is a histological micrograph of adipose tissue before deliver of longitudinal ultrasound waves. FIG. 1B is a micrograph of adipose tissue that has been damaged by longitudinal ultrasound waves. As shown in FIG. 1B, there is no "intact" adipose tissue—a large fraction of the adipocytes and of other cells are separated from the connective tissue (septae).

The following published documents are believed to represent the current state of the art and the contents thereof are hereby incorporated by reference: U.S. Pat. No. 5,549,544, U.S. Pat. No. 6,450,979, United States patent application publication 20060094988, United States patent application publication 20060241531, United States patent application publication 20070232963, and JP10263038A.

SUMMARY OF EMBODIMENTS

The present inventors are now disclosing an apparatus and method for selectively damaging adipose tissue beneath the surface of the skin by delivering transverse ultrasound waves to the adipose tissue via the skin surface. The "deeply-penetrating" transverse ultrasound waves propagate or conduct to the fibers/membrane structure (or tissue matrix) of adipose tissue to (i) deform and damage adipocytes cell membranes by repeatedly stretching and allowing to relax the cell membranes while (ii) causing substantially no collateral damage to surrounding tissue.

Histological results have indicated that immediately after application of the ultrasound waves (for example, within an half-hour), it is possible to observe at least some adipocytes that (i) have not been ruptured and are part of an intact tissue matrix but (ii) whose cell membranes have, nevertheless, been deformed—for example, having a "zig-zag" shape. Furthermore, histological results have also indicated that at a later time (for example, after one or several days) at least these adipocytes (i.e., whose cell membranes have been damaged) are later removed from the adipose tissue and the contents (for example, triglycerides) of these adipocytes have been released.

Thus, in some embodiments, the administered transverse ultrasound energy (i) induces observable adipocyte cell membrane deformation within a relatively short period of time (e.g., within about 30 min. of treatment) and (ii) is effective to trigger a biological process acting over a relatively long period of time (e.g., a few days) whereby (a) the damaged adipocytes disappear and (b) the triglycerides contained in the damaged adipocytes are slowly removed by natural metabolic and healing processes that occur over this longer period of time.

In some embodiments, the presently-disclosed ultrasound-based apparatus and methods advantageously provide a relatively "gentle" treatment employing transverse ultrasound waves where there is no requirement to mechanically rupture most adipocytes within a region of tissue at the time of treatment, but where the adipocytes are damaged by the ultrasound energy to a sufficient extent to induce their subsequent elimination by natural processes.

Various techniques are disclosed to facilitate this biological effect.

In one embodiment, the delivered transverse ultrasound energy may be 'scattered' within the treated tissue so that ultrasound energy is delivered in multiple directions at a given time rather than delivered in a single direction and/or focused to a single location. This is useful for achieving a higher success rate whereby more adipocytes within a given volume of adipose tissue are successfully damaged by the relatively low energy transverse ultrasound wave to the extent required for their eventual destruction, (without relying exclusively upon "thermal effects").

In some embodiments, this scattering of delivered energy may be provided at least in part by shape and/or surface features (and/or other features) of a convex energy-delivery surface of the ultrasound applicator or sonotrode. The terms "applicator" and "sonotrode" are used interchangeably herein.

Optionally and, in some embodiments, preferably, the transverse ultrasound waves are provided in combination with longitudinal ultrasound waves that heat the upper layers of tissue.

This may be carried out using a device that is configured to deliver both longitudinal and transverse mechanical waves of ultrasound frequency. Some embodiments of the present invention provide an ultrasound device including a 'mushroom-shaped' sonotrode configured to deliver both transverse ultrasound energy as well as longitudinal ultrasound energy from a single device.

It is now disclosed for the first time a device for treating adipose tissue located beneath a patient's skin, the device comprising: a) a sonotrode including a proximal portion, a distal portion, and an elongated neck portion connecting the proximal portion to the distal portion, the sonotrode being dimensioned such that: (i) a ratio between a dimension B of the neck portion parallel to an elongate axis of the neck and a dimension d1 of the neck portion perpendicular to the elongate axis of the neck is at least 1.5; (ii) a ratio between a dimension d2 of the distal portion perpendicular the elongate axis of the neck and a dimension C of the distal portion parallel to the elongate axis of the neck is at least 2; (iii) a ratio between a dimension D of the proximal portion perpendicular to the elongate axis of the neck and the dimension d1 of the neck portion perpendicular to the elongate axis of the neck is at least 2.5; and (iv) a ratio between the dimension d2 of the distal portion perpendicular to the elongate axis of the neck and the dimension d1 of the neck portion perpendicular to the elongate axis of the neck is at least 2; and b) an ultrasound transducer, wherein the ultrasound transducer is operatively coupled to the proximal portion of the sonotrode and induces ultrasound vibrations in the distal portion.

In some embodiments, the ultrasound transducer induces both transverse and longitudinal ultrasound vibrations in the distal portion.

In some embodiments, the ultrasound transducer and the sonotrode are configured to provide a "transverse wave mode" where at least 30%, by energy, of the induced ultrasound vibrations within the distal portion are transverse ultrasound vibrations in a direction that is substantially perpendicular to the neck axis within a tolerance of 20 degrees.

In some embodiments, the ultrasound transducer and the sonotrode are configured such that, when in the transverse wave mode, the ultrasound transducer induces mechanical vibrations in the proximal portion and/or in the neck portion that: i) are a direction that is substantially parallel within a tolerance of 20 degrees to the elongate neck axis; and ii) have a power level that is at least 70% a power level of the induced ultrasound vibrations within the distal portion.

In some embodiments, there is little or no "net momentum" in the direction perpendicular to the neck axis, even in "transverse wave mode." Thus, in some embodiments, for at least one bounding volume within the distal portion, the induced ultrasound vibrations cause motion in a plane that is perpendicular to the neck axis such that a ratio between: i) a momentum of matter within the distal portion associated with the motion in the perpendicular plane; and ii) a product between a mass within the bounding volume and a kinetic energy associated with the motion in the perpendicular plane, is at most 0.2.

In some embodiments, the ultrasound transducer and the sonotrode are configured to provide a longitudinal wave mode wherein at least 30%, by energy, of the induced ultrasound vibrations within the distal portion are longitudinal ultrasound vibrations in a direction that is substantially parallel to the neck axis within a tolerance of 20 degrees.

In some embodiments, the ultrasound transducer and the sonotrode are configured to provide both the transverse wave mode and the longitudinal wave mode such that: i) when in the transverse wave mode, the ultrasound transducer operates at a first ultrasound driving frequency; and ii) when in the longitudinal wave mode, the ultrasound transducer operates at a second ultrasound driving frequency that is different from the first ultrasound driving frequency.

In some embodiments, a difference between the first and second driving frequencies is at least 3 kHz.

In some embodiments, a ratio between: i) difference between the first and second driving frequencies; and ii) a maximum of the first and second driving frequencies is at least 0.1.

In some embodiments, i) the sonotrode and the ultrasound transducer provide both the longitudinal and the transverse wave mode; and ii) the device further comprises: c) a device controller operative to cause the sonotrode and the ultrasound transducer to: I) effect a preliminary phase of a duration having a duration $t_{HOT}$ that is at least 10 seconds and at most 30 seconds where the sonotrode and the ultrasound transducer provide the longitudinal wave mode; and II) after the preliminary phase, effect a main phase having a duration $t_{COLD}$ that is at least twice the duration $t_{HOT}$ of the preliminary phase where the sonotrode and the ultrasound transducer provide the transverse wave mode.

In some embodiments, the controller is operative to repeat the preliminary and the main phases at least 10 times.

In some embodiments, the controller is operative to commence the main phase within 15 seconds of a completion of the preliminary phase.

In some embodiments, the controller is operative such that a ratio between the duration $t_{COLD}$ of the main phase and the duration $t_{HOT}$ of the preliminary phase is at most 5.

In some embodiments, the device further comprises: c) a device controller configured to: i) effect a frequency scan by operating the ultrasound transducer at a plurality of different candidate frequencies and determining, for each given candidate frequency of the plurality of frequencies, a respective indication of a power of ultrasound waves generated by the ultrasound transducer that is associated with the given candidate frequency; ii) in accordance with the power indications, select an operating frequency from the plurality of candidate frequencies; and iii) operate the transducer at the selected frequency for at least 10 seconds.

In some embodiments, the device further comprises: c) a current source 110 for providing electrical current to transducer; and d) a device controller operative to cause said electromagnetic energy source to deliver said output electromagnetic signal as a pulsed signal having one or more pulse parameters, said pulse controller operative to effect a pulse-width modulation of the electrical current provided to transducer.

In some embodiments, the ultrasound transducer and the sonotrode are configured to deliver an energy flux via an energy delivery surface of the distal portion that is at least 7 watts/cm^2.

In some embodiments, the ultrasound transducer and the sonotrode are configured so that an energy of the induced ultrasound vibrations within the distal portion is at least 40 watts and/or at most 80 watts.

In some embodiments, i) the sonotrode includes an energy delivery surface for delivering energy of the induced ultrasound vibrations to the patient's skin; and ii) when the transducer is in operation, the energy flux is at most 30% of the maximum energy flux on the energy on the energy delivery surface at a point on the energy delivery surface where the elongate axis of the neck intersects the energy delivery surface.

In some embodiments, the transducer induces transverse ultrasound vibrations within the distal portion so as to cause an alternating pinching and pulling on at least a portion of a surface of the distal portion.

In some embodiments, i) the sonotrode includes a convex energy delivery surface for delivering energy of the induced ultrasound vibrations to the patient's skin, the energy delivery surface having an area A and a center C; and ii) a distance between the center C and a point of maximum energy flux on the energy delivery surface is at least 0.2 times a square root of the area A.

In some embodiments, the ultrasound transducer is attached to the proximal portion of the sonotrode.

In some embodiments, the sonotrode is axisymmetric about the elongate neck axis.

In some embodiments, a dimension d2 of the distal portion perpendicular to the elongate axis of the neck is less than one quarter a transverse wave mode wavelength of a material of which the sonotrode is constructed.

In some embodiments, a distal surface of the distal portion includes multiple discontinuous surfaces.

In some embodiments, a distal surface of the distal portion includes a plurality of protrusions and/or indentations or depressions positioned on the distal surface.

In some embodiments, i) the sonotrode includes an energy delivery surface for delivering energy of the induced ultrasound vibrations to the patient's skin; and ii) the energy delivery surface includes a plurality of vertical ridges positioned on energy delivery surface.

In some embodiments, i) transducer and sonotrode are configured to so that a plurality of ultrasound nodes and/or anti-nodes are produced; and ii) a distance between adjacent ridges is an integral multiple and/or a reciprocal of an integral multiple of a distance between at least one of adjacent nodes and adjacent anti-nodes.

In some embodiments, i) the sonotrode includes an energy delivery surface for delivering energy of the induced ultrasound vibrations to the patient's skin; and ii) the energy delivery surface includes a plurality of concentric circular ridges positioned on the energy delivery surface.

In some embodiments, i) the sonotrode includes an energy delivery surface for delivering energy of the induced ultrasound vibrations to the patient's skin ii) the energy delivery surface has surface properties to cause scattering of energy of the mechanical waves of an ultrasound frequency delivered from the distal surface.

In some embodiments, the sonotrode includes a convex energy delivery surface for delivering energy of the induced ultrasound vibrations to the patient's skin.

In some embodiments, an acoustic impedance of a distal portion of sonotrode is at least 5 MRayls.

It is now disclosed for the first time a method of treating adipose tissue located beneath a patient's skin, the method comprising: a) coupling the distal portion of any device disclosed herein with the patient's skin surface; and b) operating the device at an ultrasound frequency with sufficient power for the distal portion of the device to induce transverse mechanical waves of an ultrasound frequency within the adipose tissue of the patient and to deform at least a portion of the adipocytes in the adipose tissue.

In some embodiments, the method further comprises the step of operating the device at an ultrasound frequency with sufficient power for the distal portion of the device to induce longitudinal mechanical waves of an ultrasound frequency in the tissue beneath the surface of the skin to heat the tissue above body temperature.

In some embodiments, the transverse and longitudinal mechanical waves of an ultrasound frequency are each induced alternately one or more times.

In some embodiments, the energy transfer surface is coated with an impedance matching material.

In some embodiments, the impedance matching material is petroleum jelly.

It is now disclosed for the first time a method of adipocyte destruction, the method comprising the step of: delivering mechanical waves of an ultrasound frequency including transverse mechanical waves to adipose tissue beneath the dermis to trigger delayed cell death within 3 days of a majority of adipocytes residing within rectangular prism control volume of adipose tissue without rupturing within 30 minutes, any more than 10% of adipocytes residing within the control volume, wherein the control volume of adipose tissue: i) has a thickness of 1 cm, a length of 2 cm and a width of 2 cm; and ii) is located beneath the skin dermis; and iii) includes at least 40,000 adipocytes In some embodiments, no more than 5% of the adipocytes residing in the control volume of adipose tissue are ruptured by the mechanical waves of the ultrasound frequency.

In some embodiments, the mechanical waves of the ultrasound frequency are delivered in a treatment session having a duration of at most 10 minutes.

In some embodiments, the control volume of adipose tissue includes at least 50,000 adipocytes.

In some embodiments, delivery of the mechanical waves of the ultrasound frequency triggers delayed cell death within 3 days of at least 75% of the adipocytes residing within the control volume of adipose tissue.

In some embodiments, delivery of the delivered mechanical waves of the ultrasound frequency is effective to introduce undulating membrane geometry in at least 30% of the adipocytes residing in the control volume of adipose tissue.

In some embodiments, delivery of the mechanical waves of the ultrasound frequency is effective to cause an adipocyte membrane deformation in at least 30% of the adipocytes residing in the control volume of adipose tissue wherein the adipocyte membrane deformation increases membrane surface area by at least 20% without increasing adipocyte volume by more than 5%.

In some embodiments, delivery of the mechanical waves of the ultrasound frequency is effective to cause an adipocyte membrane deformation in at least 30% of the adipocytes residing in the control volume of adipose tissue wherein the adipocyte membrane deformation increases, by at least 50%, a surface area of a contiguous cell membrane portion whose mass is 15% of a total cell membrane mass.

In some embodiments, the delivered mechanical waves of the ultrasound frequency are delivered so as to alternately: a) maintain the dermis and/or the epidermis at a temperature that is at least 42 degrees Celsius and at most 50 degrees Celsius for a period of time that is at least 10 seconds; b) allow the temperature of the epidermis to drop below 35 degrees Celsius for a period of time that is at least 30 seconds.

It is now disclosed for the first time a device for inducing adipocyte destruction in a patient, the device comprising: a) a sonotrode; and b) an ultrasound transducer. operatively coupled to the sonotrode, wherein the sonotrode and the ultrasound transducer are configured such that when the sonotrode is coupled to a surface of the patient's skin, the ultrasound transducer generates mechanical waves of an ultrasound frequency including transverse waves that are delivered to adipose tissue beneath the dermis of the patient via the sonotrode for a sufficient time, at a sufficient amplitude, at a sufficient transverse wave content and with sufficient scattering to trigger delayed cell death within 3 days of a majority of adipocytes residing within a rectangular prism control volume of adipose tissue without rupturing within 30 minutes, any more than 10% of adipocytes residing within the control volume, wherein the control volume of adipose tissue: i) has a thickness of 1 cm, a length of 2 cm and a width of 2 cm; and ii) is located beneath the skin dermis; and iii) includes at least 40,000 adipocytes.

In some embodiments, the sonotrode and the ultrasound transducer are configured to deliver the mechanical waves of the ultrasound frequency for a sufficient time, at a sufficient amplitude, at a sufficient transverse wave content and with sufficient scattering such that no more than 5% of the adipocytes residing in the control volume of adipose tissue are ruptured by the mechanical waves of the ultrasound frequency.

In some embodiments, the control volume of adipose tissue includes at least 50,000 adipocytes.

In some embodiments, the sonotrode and the ultrasound transducer are configured to deliver the mechanical waves of the ultrasound frequency for a sufficient time, at a sufficient amplitude, at a sufficient transverse wave content and with sufficient scattering such that delivery of the mechanical waves of the ultrasound frequency triggers delayed cell death within 3 days of at least 75% of the adipocytes residing within the control volume of adipose tissue.

In some embodiments, the sonotrode and the ultrasound transducer are configured to deliver the mechanical waves of the ultrasound frequency for a sufficient time, at a sufficient amplitude, at a sufficient transverse wave content and with sufficient scattering such that delivery of the mechanical waves of the ultrasound frequency introduces undulating membrane geometry in at least 30% of the adipocytes residing in the control volume of adipose tissue.

In some embodiments, the sonotrode and the ultrasound transducer are configured to deliver the mechanical waves of the ultrasound frequency for a sufficient time, at a sufficient amplitude, at a sufficient transverse wave content and with sufficient scattering to cause an adipocyte membrane deformation in at least 30% of the adipocytes residing in the control volume of adipose tissue wherein the adipocyte membrane deformation increases membrane surface area by at least 20% without increasing adipocyte volume by more than 5%.

In some embodiments, the sonotrode and the ultrasound transducer are configured to deliver the mechanical waves of the ultrasound frequency for a sufficient time, at a sufficient amplitude, at a sufficient transverse wave content and with sufficient scattering to cause an adipocyte membrane deformation in at least 30% of the adipocytes residing in the control volume of adipose tissue wherein the adipocyte membrane deformation increases, by at least 50%, a surface area of a contiguous cell membrane portion whose mass is 15% of a total cell membrane mass.

In some embodiments, the device further comprises: c) a device controller operative to control transverse wave content of the delivered ultrasound waves so as to alternatively: i) maintain the dermis and/or the epidermis at a temperature that is at least 42 degrees Celsius and at most 50 degrees Celsius for a period of time that is at least 10 seconds; and ii) allow the temperature of the epidermis to drop below 35 degrees Celsius for a period of time that is at least 30 seconds.

It is now disclosed for the first time a device for treating biological tissue. The presently-disclosed device comprises: a) an ultrasound transducer configured to produce ultrasound energy; and b) an ultrasound applicator including an energy delivery surface, the ultrasound applicator and the ultrasound transducer being configured such that: i) operation of the ultrasound transducer causes the energy delivery surface to vibrate at an ultrasound frequency; ii) when the ultrasound transducer operates at a first ultrasound driving frequency, the ultrasound vibrations of the energy delivery surface are primarily normal to the energy delivery surface; and iii) when the ultrasound transducer operates at a second ultrasound driving frequency, the ultrasound vibrations of the energy delivery surface are primarily along the energy delivery surface.

In some embodiments, the energy delivery surface includes at least one of i) multiple discontinuous surfaces; ii) plurality of protrusions positioned on the energy delivery surface; iii) plurality of vertical ridges positioned on the energy delivery surface; and iv) a plurality of concentric circular ridges positioned on the energy.

In some embodiments, the energy delivery surface has surface properties to cause scattering of energy of the mechanical ultrasound waves delivered from the distal surface.

In some embodiments, ultrasound applicator and the ultrasound transducer are configured such that when the ultrasound transducer operates at the first ultrasound driving frequency, at least 80%, by energy, of the ultrasound vibrations of the energy delivery surface are normal to the energy delivery surface.

In some embodiments, ultrasound applicator and the ultrasound transducer are configured such that when the ultrasound transducer operates at the second ultrasound driving frequency, at least 80%, by energy, of the ultrasound vibrations of the energy delivery surface is along the energy delivery surface.

In some embodiments, the device further comprising: c) a device controller operative to: i) operate the ultrasound transducer at the first driving frequency for a period of time that is at least 2 seconds and at most 10 seconds; ii) after the operating at the first driving frequency operate the ultrasound transducer at the second driving frequency for a period of time that is at least two times and at most 5 times a period of time of step c(i).

In some embodiments, the device controller is further operative to: iii) repeat steps c(i) and c(ii) at least five times.

In some embodiments, c) a device controller operative to: i) operate the ultrasound transducer at the first driving frequency for a period of time that is at least 2 seconds and at most 10 seconds; ii) after the operating at the first driving frequency, operate the ultrasound transducer at the second driving frequency for at least 10 seconds and at most 60 seconds.

In some embodiments, the device controller is further operative to: iii) repeat steps a(i) and a(ii) at least five times.

It is now disclosed for the first time a method of treating biological tissue of a patient using a sonotrode including an energy-delivery surface, the method comprising: a) when the energy delivery surface is engaged to a skin surface of the biological tissue: i) effecting a first treatment phase to deliver mechanical waves of an ultrasound frequency that comprise by energy at least 80% longitudinal mechanical waves of an ultrasound frequency to the biological tissue for a period of time that lasts at least 3 seconds and at most 10 seconds during which a power density of the mechanical longitudinal waves of an ultrasound frequency delivered via the energy delivery surface is at least 5 watts/cm^2 and at most 30 watts/cm^2; and ii) following the first treatment phase effecting a second treatment phase to deliver mechanical waves of an ultrasound frequency that comprise by energy at least 80% transverse mechanical waves of an ultrasound frequency to the biological tissue for a period of time that is between two and five times the period of time of the first treatment phase during which a power density of the longitudinal mechanical waves of an ultrasound frequency delivered via the energy delivery surface is at least 5 watts/cm^2 and at most 30 watts/cm^2.

In some embodiments, the first and second treatment phases are repeated at least 10 times.

In some embodiments, during the first treatment phase, at least 20% and at most 80% of an ultrasound energy delivered from the energy delivery surface penetrates beneath the skin surface of the biological tissue.

In some embodiments, the second treatment phase, at least 10% and at most 60% of an ultrasound energy delivered from the energy delivery surface penetrates beneath the skin surface of the biological tissue.

In some embodiments, the method is carried out so that at no time during the treatment is cavitation induced for a period that is more than 10 seconds.

It is now disclosed for device for inducing adipocyte destruction in a patient, the device comprising: a) a sonotrode; and b) an ultrasound transducer operatively coupled to the sonotrode such that when the sonotrode is coupled to the skin of the patient, operation of the ultrasound transducer causes mechanical waves of ultrasound frequency to be delivered to the patient; c) a device controller for controlling the ultrasound transducer to at least in part control one or more properties of the delivered mechanical waves of an ultrasound frequency, wherein the device controller is operative to control the ultrasound transducer: i) effect a first phase where the delivered waves comprise by energy at least 80% longitudinal mechanical waves of an ultrasound frequency to the biological tissue for a period of time that lasts at least 3 seconds and at most 10 seconds during which a power density of the mechanical longitudinal waves of an ultrasound frequency delivered via the energy delivery surface is at least 5 watts/cm^2 and at most 30 watts/cm^2; and ii) following the first phase, effect a second phase where the delivered mechanical waves of an ultrasound frequency comprise by energy at least 80% transverse mechanical waves of an ultrasound frequency to the biological tissue for a period of time that is between two and five times the period of time of the first treatment phase during which a power density of the mechanical longitudinal mechanical waves of an ultrasound frequency delivered via the energy delivery surface is at 5 watts/cm^2 and at most 30 watts/cm^2.

It is now disclosed for the first time a method of treating biological tissue of a patient using a sonotrode including an energy-delivery surface the method comprising: a) when the energy delivery surface is coupled to a skin surface of the biological tissue, inducing transverse mechanical waves of an ultrasound frequency in the energy delivery surface such that, at a given time: i) at least 30% by energy of the induced mechanical transverse waves in the energy delivery surface has a propagation direction within 30 degrees of a given direction; and ii) at least 30% by energy of the delivered transverse mechanical waves has a propagation direction that differs from the given direction by at least 30 degrees.

In some embodiments, the method is carried out so that at least 20% by energy of the induced mechanical transverse waves of the ultrasound frequency is transmitted at least 15 mm beneath a skin surface.

In some embodiments, at the given time, the induced transverse mechanical waves comprises at least 30%, by energy, of all mechanical waves delivered from the energy delivery surface.

In some embodiments, the transverse mechanical waves are induced such that at least 30%, by energy, of the induced mechanical traverse waves has a propagation direction that intersects with a propagation direction of the induced transverse mechanical waves.

In some embodiments, the transverse mechanical waves are induced such that at least 30%, by energy, of the induced mechanical traverse waves has a propagation direction that intersects with a propagation direction of the induced transverse mechanical waves at a location that within 0.5 cm of the energy delivery surface.

In some embodiments, a power density of the induced mechanical waves is at least 3 watts/cm^2.

In some embodiments, the energy delivery surface is substantially convex.

It is now disclosed for the first time a device for inducing adipocyte destruction in a patient, the device comprising: a) a sonotrode; and b) an ultrasound transducer operatively coupled to the sonotrode such that when the sonotrode is coupled to the skin of the patient, operation of the ultrasound transducer causes mechanical waves of ultrasound frequency to be delivered to the patient, an energy delivery surface of the sonotrode having surface properties such that the delivered ultrasound waves have the following properties: i) at least 30% by energy of the induced mechanical transverse waves in the energy delivery surface has a propagation direction within 30 degrees of a given direction; and ii) at least 30% by energy of the delivered transverse mechanical waves has a propagation direction that differs from the given direction by at least 30 degrees.

It is now disclosed for the first time a device for inducing adipocyte destruction in a patient, the apparatus comprising: a) a sonotrode; and b) an ultrasound transducer. operatively coupled to the sonotrode, wherein the sonotrode and the ultrasound transducer are configured such that when the sonotrode is coupled to a surface of the patient's skin, the ultrasound transducer generates mechanical waves of an ultrasound frequency including transverse waves that are delivered to adipose tissue beneath the dermis of the patient via the sonotrode for a sufficient time, at a sufficient amplitude, at a sufficient transverse wave content and with sufficient scattering to trigger delayed cell death of at least some adipocytes of the adipose tissue in the patient without immediately rupturing the adipocytes.

It is now disclosed for the first time a method of adipocyte destruction in a patient, the method comprising the step of: delivering mechanical waves of an ultrasound frequency including transverse mechanical waves to adipose tissue beneath the dermis to trigger delayed cell death of at least some adipocytes of the adipose tissue in the patient without immediately rupturing the adipocytes.

It is noted that features described above as pertaining to certain embodiments may also be included in other embodiments, unless indicated to the contrary herein below.

BRIEF DESCRIPTION OF THE DRAWINGS

FIG. 5A is a micrograph of untreated adipose tissue.

FIG. 5B is a micrograph of adipose tissue immediately after treatment with ultrasound waves provided by a presently-disclosed ultrasound device in accordance with some embodiments. Deformed adipose cell membranes having a "zig-zag" conformation are circled.

FIG. 5C-5D are micrographs of adipose tissue three days after treatment with ultrasound waves provided by a presently-disclosed ultrasound device in accordance with some embodiments.

FIG. 7A displays operation in the "cold mode," which transmits primarily transverse waves. FIG. 7B displays operation in the "hot mode," which transmit primarily longitudinal waves.

FIG. 10 is an illustration of a 'control volume' of adipose tissue including a plurality of adipocytes that is located beneath the skin surface.

FIGS. 11A-11B illustrate adipocyte orientations.

FIGS. 12-13A illustrate various energy delivery surfaces via which ultrasound waves are delivered to biological tissue in multiple directions.

FIGS. 13B-13C illustrate propagation axis distributions of transverse mechanical waves delivered at a given time.

FIG. 13B illustrates induced longitudinal mechanical waves in a distal portion of an exemplary sonotrode.

Figure 1A:
FIG. 1A is a micrograph of untreated adipose tissue.

While the invention is described herein by way of example for several embodiments and illustrative drawings, those skilled in the art will recognize that the invention is not limited to the embodiments or drawings described. It should be understood that the drawings and detailed description thereto are not intended to limit the invention to the particular form disclosed, but on the contrary, the invention is to cover all modifications, equivalents and alternatives falling within the spirit and scope of the present invention. As used throughout this application, the word "may" is used in a permissive sense (i.e., meaning "having the potential to"), rather than the mandatory sense (i.e. meaning "must").

DETAILED DESCRIPTION OF EMBODIMENTS

The invention is herein described, by way of example only, with reference to the accompanying drawings. With specific reference now to the drawings in detail, it is stressed that the particulars shown are by way of example and for purposes of illustrative discussion of the preferred embodiments of the exemplary system only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice and how to make and use the embodiments.

Introductory Discussion

The claims below will be better understood by referring to the present detailed description of example embodiments with reference to the figures. The description, embodiments and figures are not to be taken as limiting the scope of the claims. It will be understood that not every feature of the presently disclosed methods and apparatuses is necessary in every implementation. It will also be understood that throughout this disclosure, where a process or method is shown or described, the steps of the method may be performed in any order or simultaneously, unless it is clear from the context that one step depends on another being performed first.

Embodiments of the present invention provide an apparatus (for example, see FIG. 4) and method for selectively damaging adipose tissue below the skin surface by delivering transverse mechanical waves of an ultrasound frequency using a sonotrode (for example, see element 140 of FIG. 4) having a convex energy delivery surface 180 in contact with the skin surface.

In some embodiments, the delivered transverse ultrasound waves (i) induce mechanical motion within the adipose tissue in a direction that is perpendicular to the wave propagation direction; (ii) selectively propagate through the fibers/membrane matrix of the adipose tissue without substantially penetrating into the liquid fraction of adipose tissue (or other biological tissue); and (iii) irreversibly damage adipocytes by deforming the adipocytes' cell membranes.

In some embodiments, the relatively "low energy" delivered transverse ultrasound waves are useful for selectively damaging adipocytes while causing little or no damage to other structures in the biological tissue.

Not intending to be bound by any particular theory, it is postulated that the delivered transverse ultrasound waves which propagate within the fibers/membrane matrix of the biological tissue repeatedly stretch cell membranes of different types of cells, including but not limited to adipocytes. However, due to the biological properties of the adipocytes, the repeated stretching of adipocyte membranes deforms the adipocytes membranes and triggers delayed cell death of the adipocytes without substantially triggering cell death of other types of cells.

Thus, in experiments conducted by the present inventors, it has been observed that the delivered transverse ultrasound energy may selectively damage the adipose tissue while, causing substantially no collateral damage to other tissues (e.g., blood vessels, connective tissue, dermis, etc) (see FIG. 5D which illustrates intact nerve and blood vessels surrounded by damaged fat tissue).

Furthermore, it has been found that (i) for at least some adipocytes within adipose tissue below the dermis, the delivered transverse ultrasound energy may injure or damage at least some adipocytes within adipose tissue below the dermis without immediately rupturing them and without destroying the adipose tissue matrix in which these damaged adipocytes reside (see, e.g., see FIG. 5B), and (ii) after a certain period of time (for example, one or more days), the damaged adipocytes are broken down and removed from the adipose tissue (see, e.g., FIG. 5C).

Experimental work has indicated that most adipocytes are damaged without being immediately ruptured following application of transverse ultrasound energy according to one or more presently-disclosed teachings. Nevertheless, it will be appreciated that, in some embodiments, some adipocytes within the adipocyte tissue may also be immediately ruptured by the applied ultrasound energy.

Figure 9A:
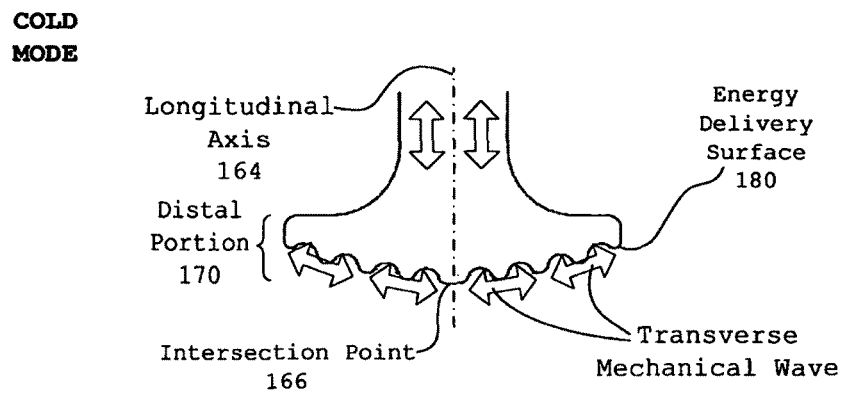
FIGS. 9A-9C illustrate induced transverse mechanical waves in a distal portion of an exemplary sonotrode according to one model.
Figure 9B:
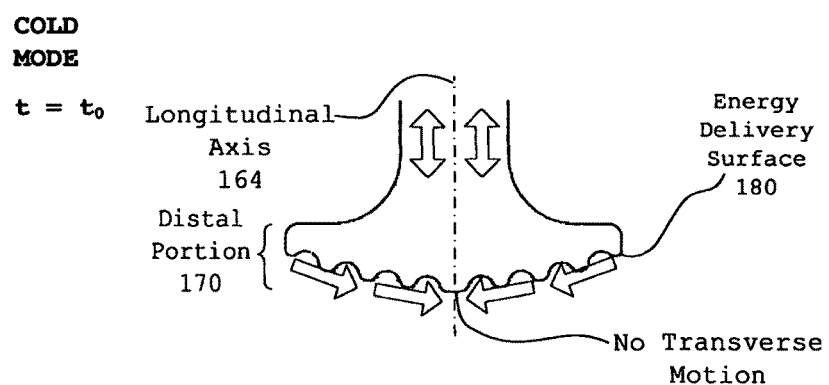
Figure 9C:
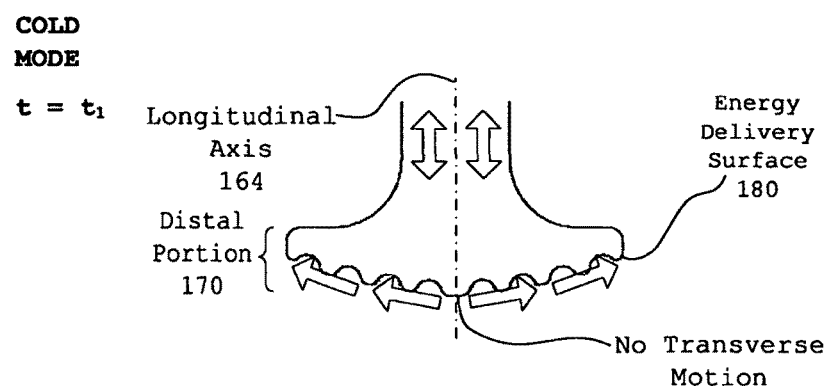

In some embodiments, the transverse mechanical waves of an ultrasound frequency are delivered using a mushroom shaped applicator or sonotrode (see for example, FIGS. 7A-7B) having a contactable "energy delivery surface" that is induced to vibrate in a "transverse wave mode." (i.e., substantially perpendicular to the longitudinal axis 164) (one theoretical model describing behavior of the sonotrode is presented with reference to FIGS. 9A-9C). When this energy delivery surface 180 is coupled to the skin of the biological tissue (i.e., brought into direct contact or indirect contact), "deep penetrating" transverse mechanical waves are delivered into the biological tissue to the adipose tissue.

Not intending to be bound by any particular theory, it is noted that in some embodiments, the delivered transverse mechanical waves are relatively low energy mechanical waves that induce little or no cavitation in the biological tissue and do not significantly damage cells of the "higher tissue layers" (i.e., layers between the adipose tissue and the surface of the skin) through which they pass en route to the adipose tissue. Therefore, the transverse mechanical waves may be said to specifically target the adipose tissue.

In some embodiments, it is useful to scatter the mechanical waves of ultrasound frequency and/or provide a relatively uniform delivery of the mechanical waves in the biological tissue. These techniques may be useful for controlling and/or increasing the success rate or efficiency at which adipocytes are damaged to an extent necessary to trigger delayed cell death of targeted adipocytes. Various techniques for facilitating the scattering and/or uniform delivery of the transverse mechanical waves are disclosed herein.

In one embodiment, rather than delivering ultrasound energy in substantially a single direction (for example, via a planar or "flat" energy delivery surface) so that at a given time the propagation axes of delivered transverse mechanical waves of ultrasound frequency are substantially parallel to each other, it may be useful to "scatter" the transverse mechanical waves of ultrasound frequency within the treated tissue. One example of this is illustrated in FIGS. 12 and 13A where the propagation axes are labeled by element 270 and where scattering may be provided by sonotrode geometry and/or surface properties of the energy delivery surface 180 via which ultrasound waves are delivered. As illustrated in FIGS. 12-13A, at least some axes 270 of propagation of transverse mechanical waves of ultrasound frequency propagating within the biological tissue are not parallel to each other.

In some embodiments, the energy delivery surface 180 is shaped so that it includes multiple discontinuous surfaces and/or a plurality of protrusions (see for example, concentric ridges 182 and/or indentations/depressions. This may be useful for facilitating the "scattering" of the transverse mechanical waves into the tissue (for example, compare FIGS. 12 and 13A).

Not intending to be bound by any particular theory, it is noted that in many clinical situations the targeted adipocytes are non-spherical and are not necessarily oriented in the same orientation (see, for example, element 292 of FIG. 11B).

By "distributing" the orientations of the propagation axes of the delivered transverse mechanical waves, it is possible to increase the likelihood that a given adipocyte is subjected to a transverse mechanical wave of ultrasound frequency at an incident angle most likely to cause maximal damage to the adipocyte (for example, at a direction substantially perpendicular to the longitudinal axis of an elongated adipocyte).

Figure 18:
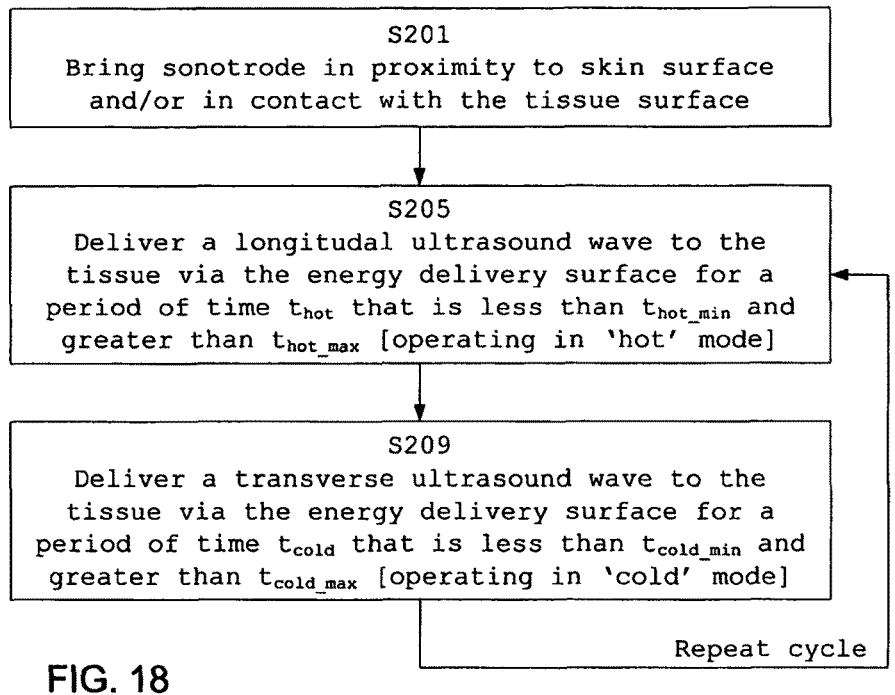
FIG. 18 is a flow chart of a 'hybrid routine' for delivering both transverse and longitudinal mechanical waves of an ultrasound frequency.
Figure 19:
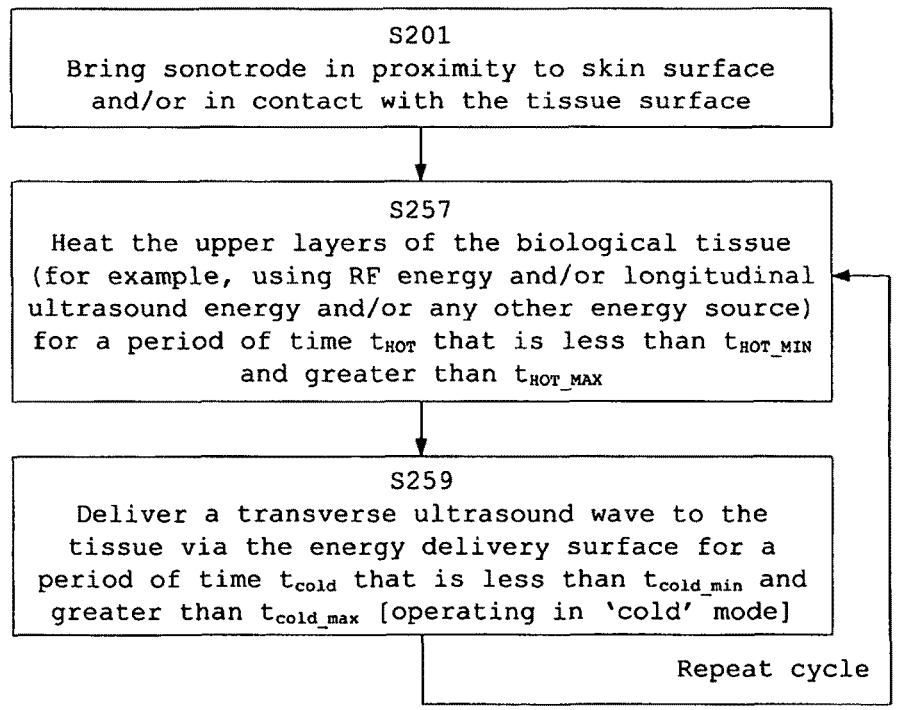
FIG. 19 is a flow chart of a treatment routine including a preliminary phase where biological tissue is pre-heated and a main phase where transverse mechanical waves of an ultrasound frequency are delivered.

In some embodiments, it may be useful to preheat upper layers of the biological tissue before delivering the transverse mechanical waves of an ultrasound frequency (for example, see FIGS. 18-19). This may be useful for improving the acoustic conductivity of the upper layers of tissue for mechanical waves of an ultrasound frequency, allowing the transverse mechanical waves to penetrate deeper or more effectively into the biological tissue, or to allow a greater fraction of the energy to penetrate to a given depth in the tissue. In some embodiments, preheating is also useful for improving the energy-absorbing properties of the tissue so that a higher fraction of energy of transverse mechanical waves is absorbed (and a lower fraction reflected).

In one embodiment, the preheating is provided using RF energy (see, for example, FIG. 19).

In yet another embodiment, the preheating is carried out by delivering longitudinal ultrasound waves to the biological tissue, for example, via the same energy delivery surface 180 used for delivering transverse mechanical waves of ultrasound frequency.

Figure 4:
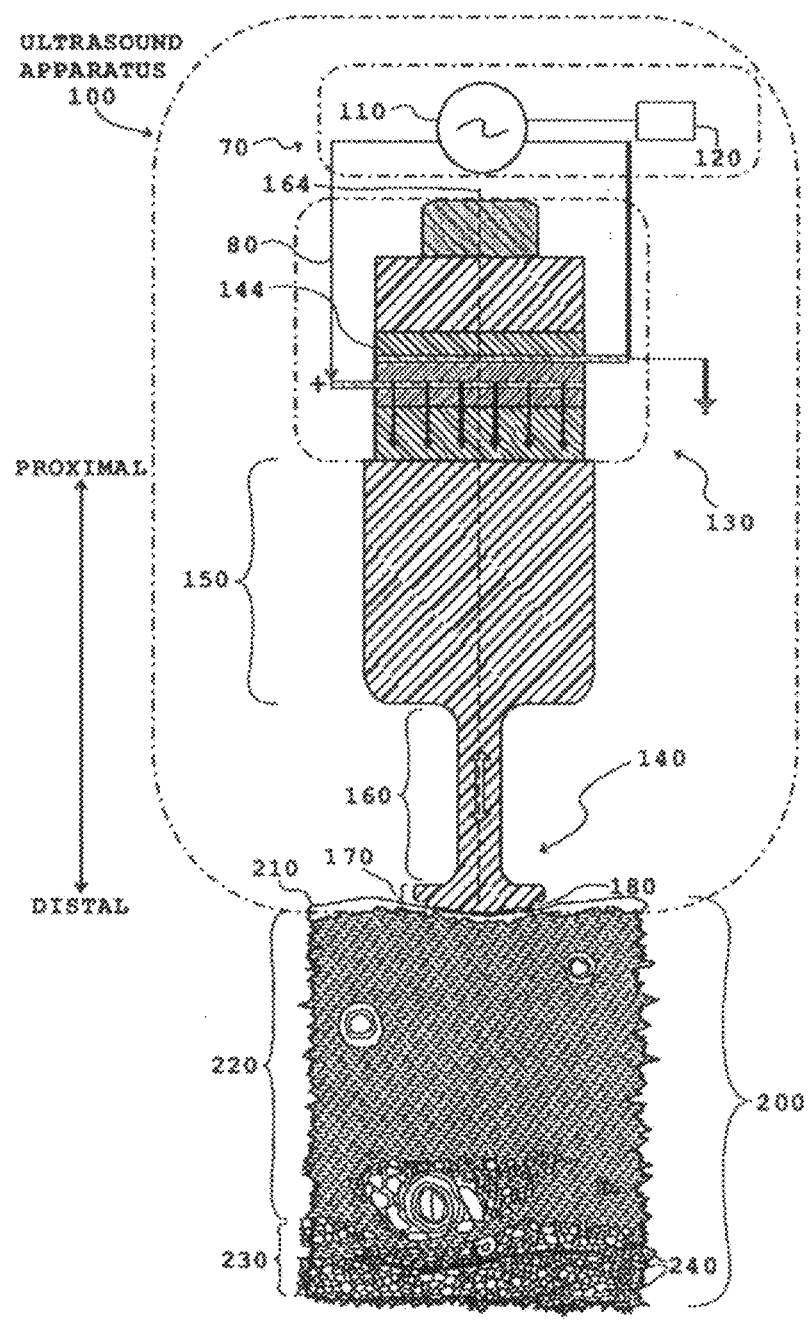
FIG. 4 is a schematic diagram of an apparatus for treating adipose tissue with ultrasound energy.
Figure 7A:
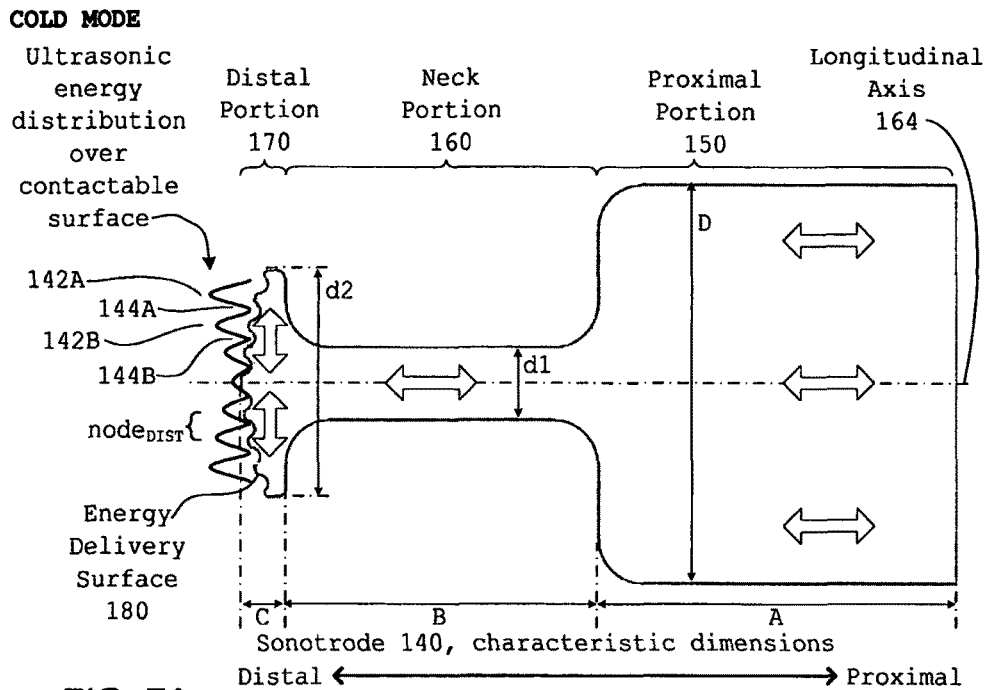
FIGS. 7A-7C are illustrations of an exemplary 'mushroom-shaped' ultrasound applicator according to some embodiments.

Thus, in some embodiments, the "mushroom-shaped" sonotrode 140 of FIGS. 4 and 7A is assembled with an ultrasound transducer 130 operatively coupled to the proximal portion of the sonotrode (e.g., attached to and/or located on the proximal portion 150). In these embodiments, distal portion 170 of the sonotrode may behave as a resonator having at least two vibration modes. In a first "bending" mode associated with a first "driving" frequency of the ultrasound transducer, a transverse standing wave of ultrasound frequency is generated within distal portion 170 (for example, see FIGS. 8, 9A-9C and 17A). Engaging sonotrode 140 to a skin surface when in this first mode (also called the "cold" mode or "traverse wave" mode) is useful for inducing transverse mechanical waves in the biological tissue beneath the skin.

Figure 16:
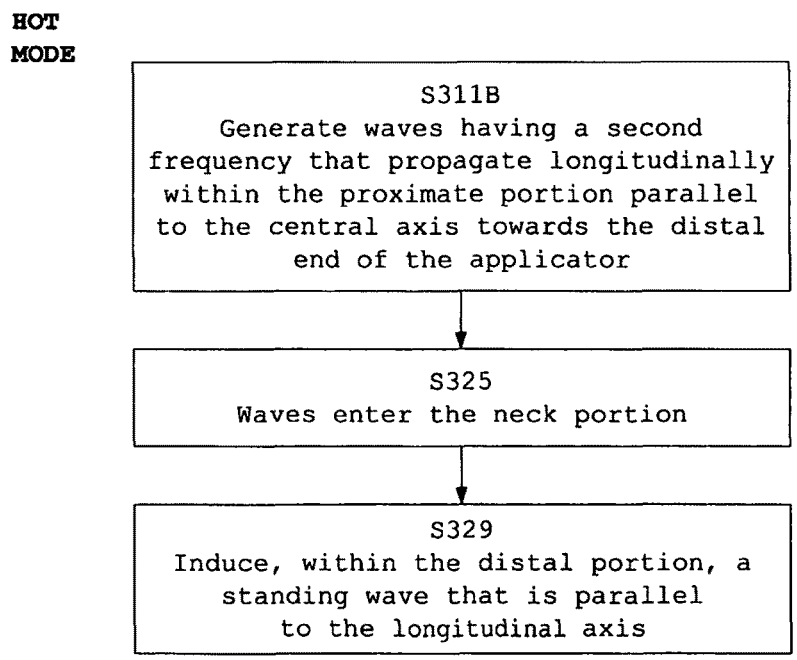
FIGS. 16, 17B are flow charts of an exemplary routines for generating longitudinal ultrasound waves within a mushroom-shaped ultrasound applicator/sonotrode while the ultrasound device is in 'hot mode.'
Figure 17A:
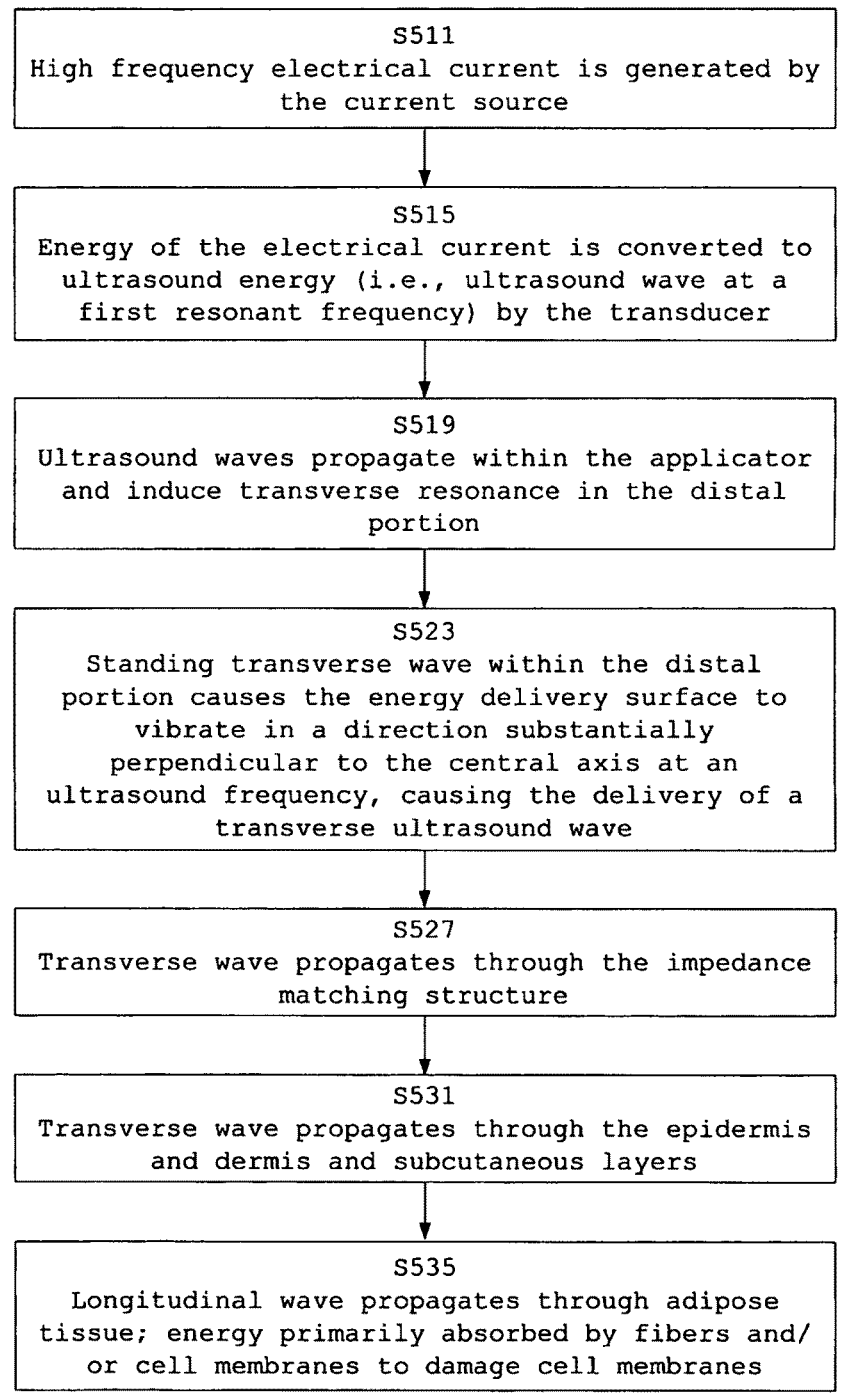
FIG. 17A is a flow chart of an exemplary routine for generating transverse ultrasound waves within a mushroom-shaped ultrasound applicator/sonotrode while the ultrasound device is in 'cold mode.'
Figure 17B:
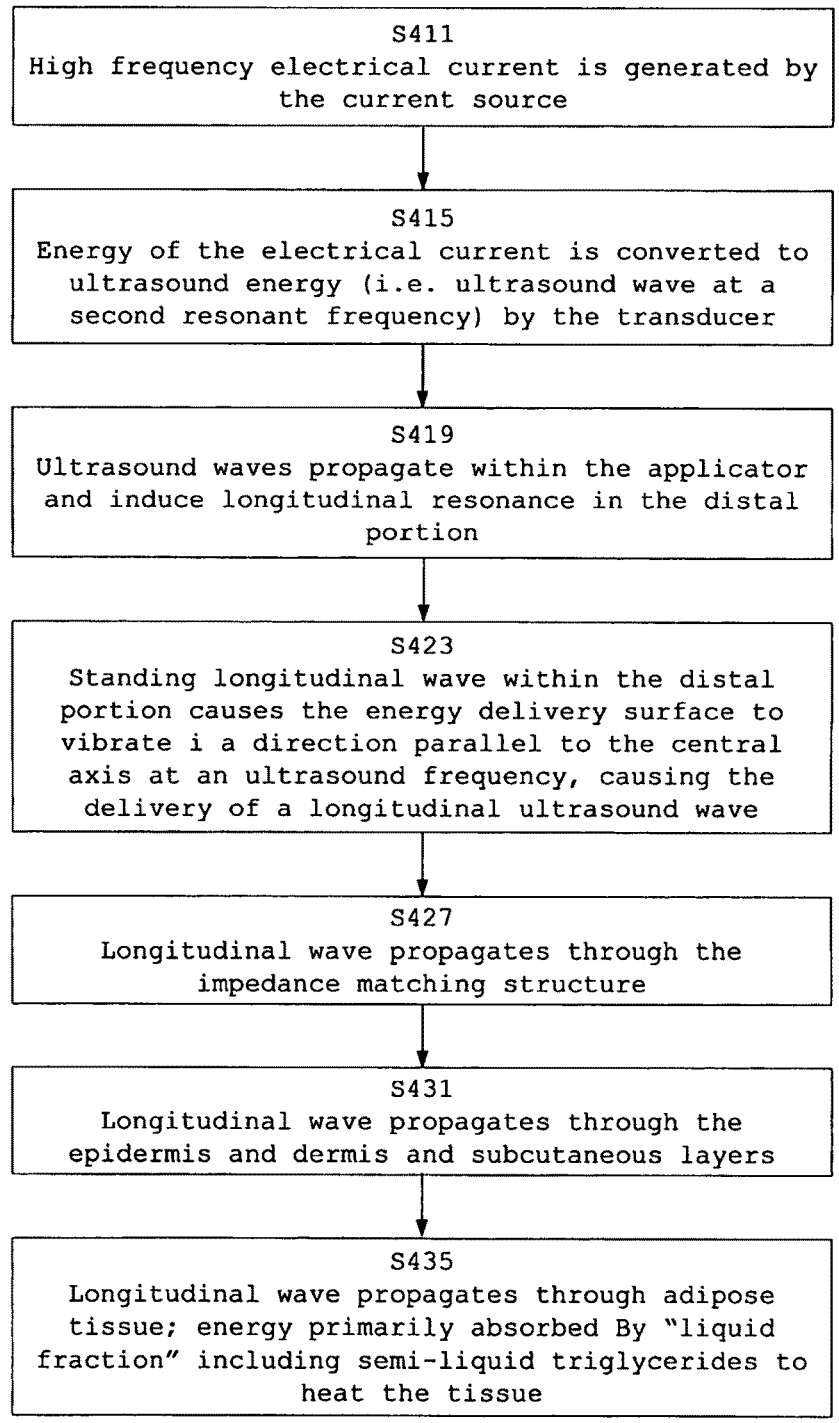

In a second "plunger" mode (also called "hot" mode or "longitudinal wave" mode) associated with a second "driving" frequency of ultrasound transducer 130, a longitudinal standing wave of ultrasound frequency is generated within distal portion 170 (for example, see FIGS. 16 and 17B). Coupling sonotrode 140 to a skin surface when in the second or "hot" mode is useful for inducing longitudinal mechanical waves (i.e., longitudinal ultrasound waves) in the biological tissue beneath the skin. In some embodiments, the longitudinal ultrasound waves are useful for preheating the upper layers of biological tissue.

Figure 15A:
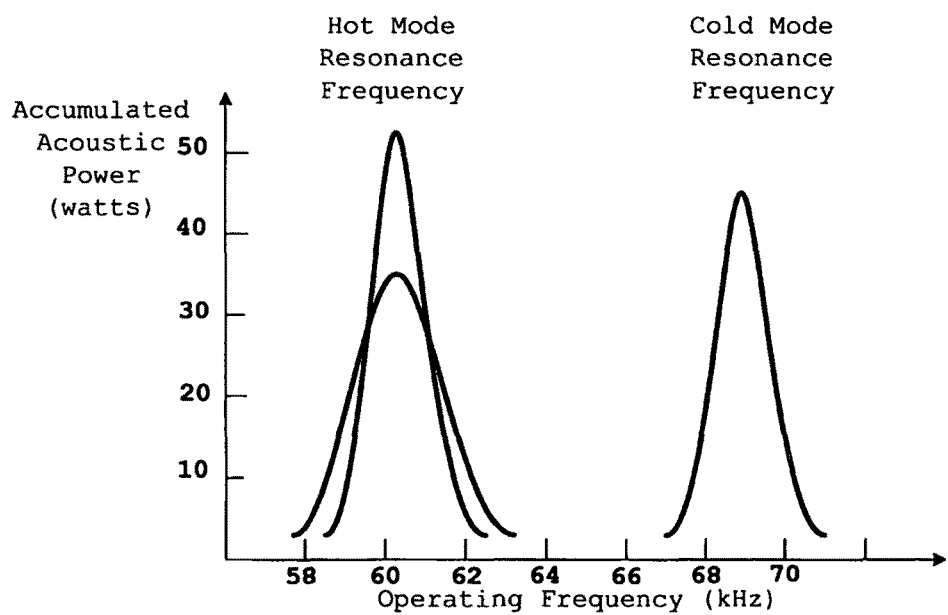
FIGS. 15A-15B illustrate 'hot mode' and 'cold mode' resonance frequencies of a 'mushroom-shaped' ultrasound applicator/sonotrode.

FIG. 15A illustrates exemplary resonance frequencies for one particular non-limiting ultrasound applicator or sonotrode (e.g., 140 of FIG. 7A). The x-axis of the graph of FIG. 15A is the operating frequency, and the y-axis is the acoustic power in the transducer and the sonotrode.

Figure 14:
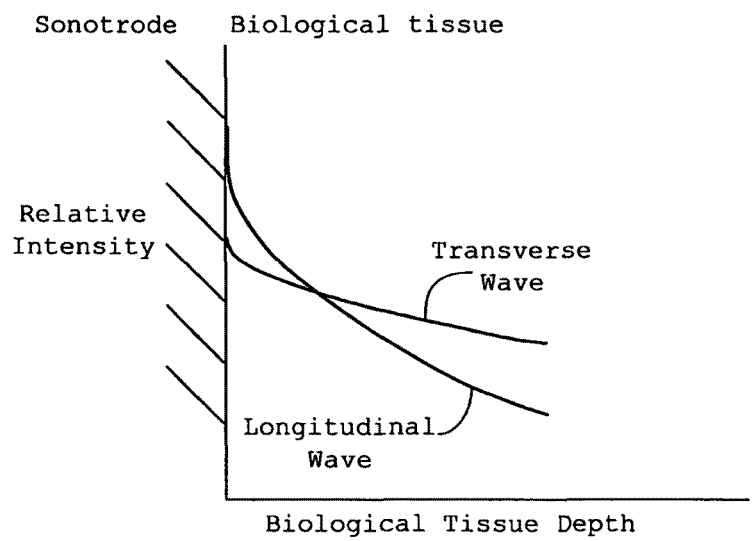
FIG. 14 illustrates intensities of transverse waves and longitudinal waves as a function of depth within biological tissue.

As illustrated in FIG. 14, typically the transverse ultrasound waves are deeper-penetrating than the longitudinal ultrasound waves, and have a lower rate of absorption.

Not intending to be bound by theory, it is noted that, in some embodiments, (i) longitudinal waves are generally transmitted through the liquids of the tissue and may generate cavitation in the upper layers of tissue and (ii) transverse waves pass through the upper layers, are absorbed mostly by the fiber matrix of the deeper adipose tissue, and do not generate cavitation.

Because the longitudinal waves are better absorbed by the upper layer of tissues, they do not penetrate as deeply (as is shown in FIG. 14), and hence, are useful for heating the upper layers of tissue.

Various "hybrid" treatment protocols include a first "preliminary" treatment phase where the mechanical waves of an ultrasound frequency are primarily longitudinal ultrasound waves and a second "main" treatment phase where the mechanical waves of an ultrasound frequency are primarily transverse waves are disclosed herein (see, for example, FIGS. 18 and 19 and the accompanying discussion). In some embodiments, the multimode ultrasound device (i.e., an ultrasound device capable of operating in both a "cold mode" and "hot mode" as described herein) includes an electronic controller (see element 120 of FIG. 4) that is programmed to provide one or more presently-disclosed protocols.

Although not a limitation, it is noted that in some embodiments, the mechanical waves are of a low ultrasound frequency—for example, below 100 kHz, or below 80 kHz.

For the present disclosure, the terms "applicator" and "sonotrode" are used interchangeably herein.

For the present disclosure, "ultrasound waves" refers to mechanical waves of an ultrasound frequency—i.e. at least 20 kHz.

Thus, ultrasound waves may refer either to (i) longitudinal mechanical waves of ultrasound frequency; or (ii) transverse mechanical waves of ultrasound frequency. Thus, the terms "ultrasound waves" and "mechanical waves of an ultrasound frequency" are used interchangeably herein.

For the present disclosure, "ultrasound vibrations" refers to any mechanical vibrations of an ultrasound frequency. Thus, the terms "ultrasound vibrations" and "mechanical vibrations of an ultrasound frequency" are used interchangeably herein.

As noted earlier, the terms "applicator" and "sonotrode" are used interchangeably herein.

The presently-disclosed teachings may be used to treat adipocytes in any location of the body, including but not limited to the abdomen region, the buttocks and the thighs.

Some of the presently disclosed embodiments relate to a technique and device for "selectively" damaging adipocytes using ultrasound energy—i.e., damaging of adipocytes while causing little or no damage to proximate tissues (e.g., blood vessels, connective tissue, dermis, nerve tissue, etc). There is no requirement of selectively targeting certain "targeted adipocytes" more than other "non-targeted adipocytes."

In the present disclosure, when the sonotrode 140 and/or ultrasound transducer 130 and/or controller 120 are "configured" or "operative" to provide a certain feature of delivered ultrasound waves (or a feature of ultrasound vibrations within or on the sonotrode or a portion thereof, or a certain "momentum" feature of the sonotrode), this means that any suitable set of device parameters familiar to one skilled in the art may be used. In different non-limiting examples, these device parameters may relate to sonotrode geometry and/or sonotrode material properties and/or 'surface properties' of an energy delivery surface of the sonotrode 140 and/or ultrasound transducer power levels and/or ultrasound frequency and/or one or more pulse parameters and/or any other structural parameter familiar to the skilled artisan. It will be appreciated that the above list is intended as exemplary and not as limiting.

The feature(s) of the delivered ultrasound may be defined in any appropriate manner—for example, in terms of fraction of total ultrasound energy that is energy of longitudinal and/or transverse ultrasound waves, direction(s) of wave propagation, in terms of the effect that the delivered ultrasound has upon biological tissue subjected to the delivered ultrasound or in any other manner recognizable to the skilled artisan.

Figure 2:
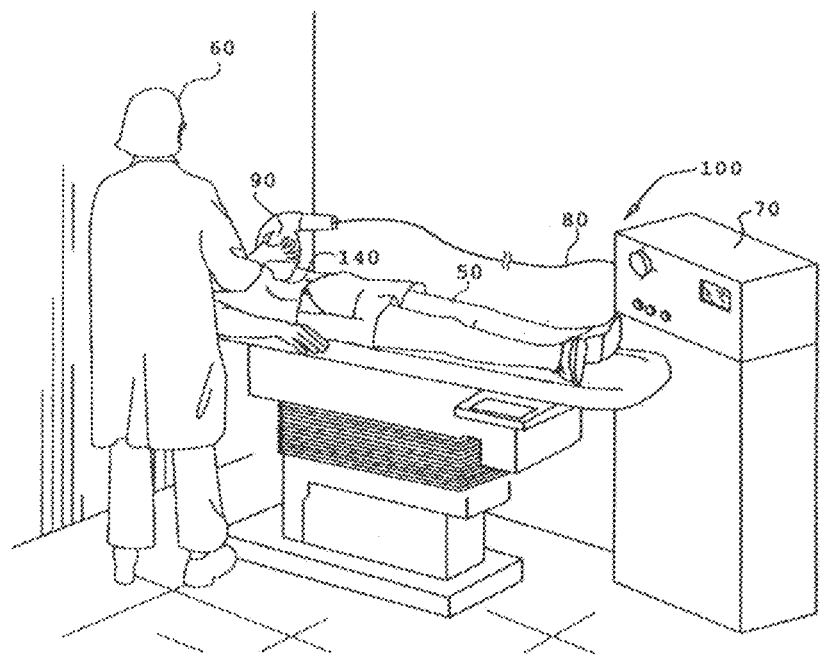
FIG. 2 is a schematic, pictorial illustration of an apparatus for treating adipose tissue with ultrasound energy, in accordance with an embodiment of the present invention.
Figure 3:
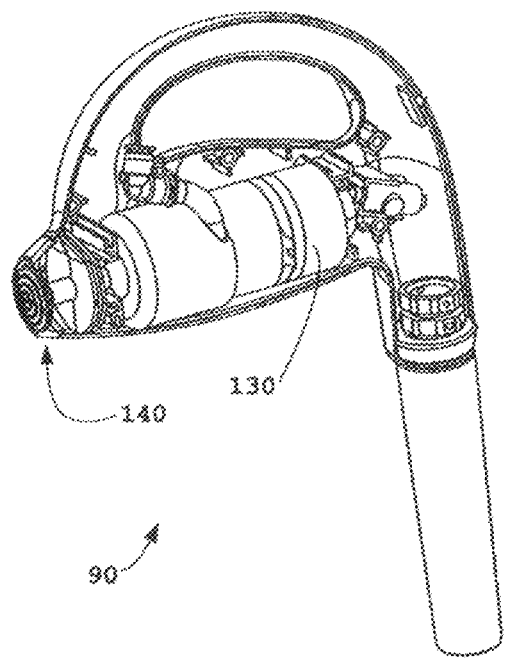
FIG. 3 is a schematic cutaway view of a handpiece of an apparatus for treating adipose tissue with ultrasound energy, in accordance with an embodiment of the present invention.

A Discussion of FIGS. 2-3: Apparatus 100 Associated with Handpiece 90

FIG. 2 is a schematic, pictorial illustration of an apparatus 100 for treating adipose tissue with ultrasound energy, in accordance with an embodiment of the present invention. As illustrated in FIG. 2, at least a portion of apparatus 100 is mechanically integrated with handpiece 90.

In the example of FIG. 2, operator 60, such as a physician, operates apparatus 100. In particular, operator 60 may (i) couple ultrasound sonotrode 140 of handpiece 90 to the skin of a patient 50 and (ii) move the sonotrode 140 over the skin of the patient using handpiece 90. As illustrated in FIG. 2, a control console 70 supplies electrical energy to device 90 via a cable 80.

FIG. 3 is a schematic, cutaway view of handpiece 90, in accordance with some embodiments. Electrical current carried by cable 80 is fed to ultrasound transducer 130, which provides ultrasound energy to sonotrode 140. Further details are presented hereinbelow.

Discussion of FIG. 4—A Brief Overview of Ultrasound Apparatus 100

FIG. 4 is an illustration of an apparatus 100 for delivering ultrasound energy to biological tissue 200 according to some embodiments. The apparatus 100 includes: (i) an ultrasound transducer 130 (for example, a piezo-ceramic transducer or a magnetostrictive-type ultrasound transducer or a transducer of any other type) for producing ultrasound energy at one or more frequencies; and (ii) a sonotrode 140 or ultrasound applicator 140 configured to deliver ultrasound energy (i.e., transverse mechanical waves of an ultrasound frequency and optionally longitudinal ultrasound waves) provided by ultrasound transducer 130 to the biological tissue 200 via an energy delivery surface 180 in contact with biological tissue 200.

In the non-limiting example of FIG. 4, sonotrode 140 is a mushroom-shaped ultrasound applicator including a proximal portion 150 connected to a distal portion 170 via neck portion 160. As will be discussed below with reference to FIGS. 7A-7B, sonotrode 140 is configured so that distal portion 170 behaves as a resonator. Thus, when transducer 130 produces ultrasound energy at one of the "driving frequencies," it induces transverse mechanical vibrations in the distal portion 170 in a direction that is substantially perpendicular to longitudinal axis 164. Inducing these transverse mechanical vibrations in the distal portion 170 at a time that energy delivery surface 180 of sonotrode 140 is engaged with, or coupled to an upper surface of epidermis 210 causes transverse mechanical waves of an ultrasound frequency to be delivered to the biological tissue 200.

As discussed below with reference to FIGS. 7A-7B, 15A-15B, in some embodiments, apparatus 100 is a multi-mode device that is configured, (i) to deliver primarily transverse ultrasound energy to biological tissue 200 when in a first, cold mode, and (ii) to deliver primarily longitudinal transverse energy to biological tissue 200 when in a second, hot mode. The second mode or 'hot mode' is useful for heating at least a portion of the biological tissue (for example, upper layers of tissue), while in the first mode or 'cold mode,' the biological tissue may not be heated at all and/or heated only minimally.

The delivered transverse mechanical waves of ultrasound frequency travel to the adipocytes 240 of adipose tissue 230 via epidermis 210 and dermis 220, causing no, or only relatively minimal, collateral damage to the layers of tissue above the adipose tissue 230.

As shown in FIG. 4, energy delivery surface 180 of sonotrode 140 is a substantially convex surface (e.g., having a hemispherical shape). As discussed below with reference to FIGS. 8-9C, this may be useful for scattering incident ultrasound waves at different angles within the treated biological tissue.

In some embodiments, a 'dynamic' or 'in-motion' treatment technique is applied, whereby ultrasound applicator 140 is moved transversally over the surface of biological tissue 200 (for example, at a minimal speed of 0.5 cm/sec or 1 cm/sec or 2 cm/sec or 3 cm/sec for a minimum distance that is at least 5 cm or 10 cm or 15 cm) as transverse and/or longitudinal ultrasound waves are delivered to biological tissue 200. The movement of the applicator 140 over the treated tissue may be useful for improving energy coupling such as by generating a pressure between the applicator 140 (i.e., energy delivery surface 180) and the tissue. This may provide a better ultrasound coupling, and is useful for facilitating and ensuring treatment of the entire region sought to be treated.

In some embodiments, some sort of petroleum jelly (for example, Vaseline®) may be applied to energy delivery surface 180. This may be useful for reducing dynamic friction between energy delivery surface 180 and the upper surface of biological tissue 200. Furthermore, as discussed below, in some embodiments it is desirable to improve acoustic coupling between applicator 140 and biological tissue 200 (i.e., to reduce the amount of reflected power), and Vaseline may be useful for this purpose as well. Thus, in some embodiments, petroleum jelly fills up the voids between the applied sonotrode surface and biological tissue, "replacing" the air, and improving acoustic impedance matching of the system. This may decrease the fraction of ultrasonic power that is reflected.

As illustrated in FIG. 4, the apparatus 100 of FIG. 4 may also include (i) a reflector 144 for reflecting generated ultrasound energy downwards (the reflector is usual part of ultrasonic transducer) towards the biological tissue 200; (ii) a current source 110 for powering transducer 130 and (iii) a device controller 120 for modulating the electrical power delivered to transducer 130 (for example, for controlling the amplitude and/or frequency of transducer 130 and/or for controlling one or more pulse parameters in the event that transducer 130 generates pulsed ultrasound energy).

In some embodiments, the apparatus 100 also includes a mechanism for epidermal cooling to minimize or eliminate pain.

It is noted that device controller 120 may be implemented in any combination of electrical circuitry and executable code modules. In some embodiments, device controller 120 may include one or more elements depicted in FIG. 21.

Although current source 110 and controller 120 are drawn in close proximity of sonotrode 140 in FIG. 4, this is not a requirement. In some embodiments, current source 110 and/or controller 120 are attached to and/or associated with console 70 (see FIG. 2).

Discussion of Impedance Matching in the Apparatus of FIG. 4

In some embodiments, one or more features are provided to facilitate matching of acoustic impedances between applicator 140 and biological tissue 200.

Although sonotrode 140 may be constructed of any material, in some embodiments, materials having relatively lower acoustic impedance (i.e., that are relatively close to the 2-2.5 MRayls acoustic impedance of biological tissue) are chosen. Thus, in some embodiments, applicator or sonotrode 140 is constructed primarily or exclusively of aluminum (or an alloy thereof) having an acoustic impedance of about 17 MRayls rather than titanium, which has an acoustic impedance of about 27 MRayls. Alternatively or additionally, plastic materials (for example, having an acoustic impedance that is greater than the acoustic impedance of biological tissue but less than the acoustic impedance of aluminum) may be used.

It is appreciated that the above list of materials is intended as illustrative and not as limiting.

Not desiring to be bound by any particular theory, it is appreciated that, in some embodiments, the acoustic impedance of sonotrode 140 should not be too low, since, in certain some embodiments; the acoustic impedance of ceramic of transducer 130 may be about 40 MRayls. Thus, in some embodiments, sonotrode 140 (or a portion thereof—for example, proximal, neck or distal portions) may have an acoustic impedance of at least 5 MRayls or at least 7.5 MRayls or at least 2 or 3 times an acoustic impedance of biological tissue).

In some embodiments, even though applicator 140 and energy delivery surface 180 are in close contact with an upper surface of biological tissue 200, there still may be some atmospheric air layer between the two. Thus, in some embodiments, and as discussed above, a material having an intermediate acoustic impedance (for example, a petroleum jelly such as Vaseline®) that is greater than the acoustic impedance of biological tissue but less than the acoustic impedance of the applicator is applied to energy delivery surface 180.

Furthermore, in some embodiments, energy delivery surface 180 may be coated with a substance (for example, a plastic or Teflon®, or alumina) useful for facilitating matching of acoustic impedance.

In one example, sonotrode 140 is constructed of aluminum with an alumina coating.

Discussion of Mechanical Properties of Sonotrode 140

Not wishing to be bound by any particular theory, it is noted that, in some embodiments, it is desirable to construct sonotrode 140 of a relatively "rigid" material that is less likely to absorb ultrasound vibrations in the form of heat. Thus, in some embodiments, sonotrode 140 (or proximal and/or neck and/or distal portion) is constructed primarily of a material which is relatively "rigid"—for example, (i) a material having a tensile strength that is at least about 10,000 or 15,000 or 20,000 or 25,000 or 30,0000 or 40,000 or 50,000 psi (which is at least about 70 or 105 or 140 or 175 or 210 or 245 or 280 MPa) and/or (ii) a material having a shear strength that is at least about 15,000 or 20,000 or 25,000 or 30,000 or 40,000 or 50,000 psi (which is at least about 105 or 140 or 175 or 210 or 280 or 350 MPa).

Furthermore, in some embodiments, in order reduce the likelihood of a "mechanical softening" of sonotrode 140, sonotrode 140 (or proximal and/or neck and/or distal portion) is constructed primarily of a material having a relatively "high" melting point—for example, at least 300 degrees Celsius or at least 400 degrees Celsius or at least 500 degrees Celsius.

Furthermore, in some embodiments, in order to facilitate cooling of sonotrode 140 (for example, using cold water), it is desirable to construct sonotrode 140 of a relatively thermally conductive material. Thus, in some embodiments, sonotrode 140 (or proximal and/or neck and/or distal portion) is constructed primarily of a material with a relatively "large" thermally conductivity—for example, at least 5 W m$^{-1}$ K$^{-1}$ or at least 10 W m$^{-1}$ K$^{-1}$ or at least 20 W m$^{-1}$ K$^{-1}$ or at least 50 W m$^{-1}$ K$^{-1}$ or at least 100 W m$^{-1}$ K$^{-1}$ or at least 200 W m$^{-1}$ K$^{-1}$.

In some embodiments, proximal 150, neck 160 and distal 170 portions of sonotrode 140 are 'integrally formed' with each other, as opposed to glued together or fastened together.

Discussion of FIGS. 5A-5C—Histological Results Related Treating Adipose Tissue with Transverse Ultrasound Waves FIGS. 5A-5C are micrographs of subcutaneous adipose tissue: (i) before ultrasound damage (see FIG. 5A); (ii) immediately after ultrasound damage by transverse ultrasound mechanical waves (i.e., within 30 minutes; see FIG. 5B); and (iii) three days after the ultrasound damage by transverse ultrasound mechanical waves (see FIG. 5C).

Figure 1B:
FIG. 1B is a micrograph is a adipose tissue immediately after treatment with longitudinal ultrasound waves.

In contrast to FIG. 1B, where adipocytes and other surrounding tissue are damaged non-selectively by the longitudinal ultrasound waves (i.e., causing extensive collateral damage to cells other than adipocytes), in cells of FIG. 5B, the damage is substantially confined to adipocytes only.

Figure 25A:
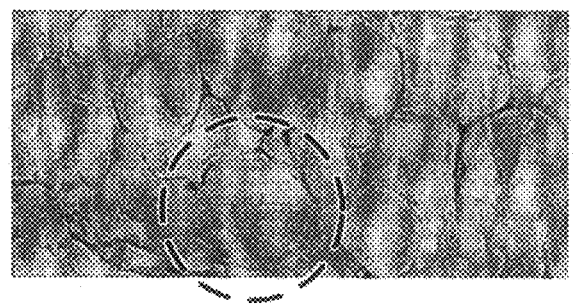
FIGS. 25A-25B are micrographs of damaged adipocytes.
Figure 25B:
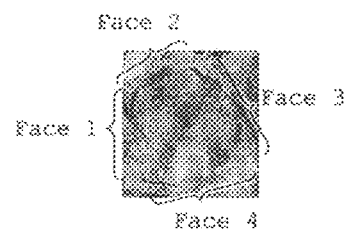

As shown in FIG. 5B, the stretching and/or compressing of cell membranes by the transverse mechanical waves of ultrasound frequency causes a "zig-zag" pattern that (i) introduces undulating membrane geometry (see, for example, the portions of cell membranes within the white ovals) to cell membranes of the adipocytes and (ii) increases the surface area of the cell membranes (see also FIGS. 25A-25B).

Although the adipocytes in FIG. 5B have been damaged by the transverse mechanical waves of ultrasound frequency, the cells are not ruptured but alive at the time immediately after (i.e., less than 30 minutes after) administration of the transverse mechanical waves. Furthermore, in contrast to the situation in FIG. 1B where there is extensive damage of both adipocytes and other structures caused by longitudinal ultrasound waves, the damage in the example of FIG. 5B appears to be substantially confined to adipocytes only, thereby providing selective treatment.

Although the cells are not ruptured and are alive in FIG. 5B, the adipocyte cell membrane deformation damage by the ultrasound energy is effective for triggering a delayed cell death process whereby the adipocytes are eventually (e.g., within 3 days) broken down by biological pathways, as evidenced in FIG. 5C.

Not intending to be bound by any theory, it is noted that by triggering a process whereby adipocytes are removed over hours or days rather than instantly ruptured, it may be possible to facilitate metabolism and eventual excretion of the fatty liquid content of the adipocytes.

The presence of adipocytes that are damaged but not ruptured (for example, a majority of cells within a 'control volume' as discussed with reference to FIG. 10), does not imply absolutely no cells will be immediately ruptured when the adipose tissue is subjected to mechanical waves of ultrasound frequency. As noted earlier, in some embodiments, a small number (e.g., less than 50% but generally less than about 20%) of adipocytes within the adipocyte tissue may also be immediately ruptured by the applied ultrasound energy.

Figure 6A:
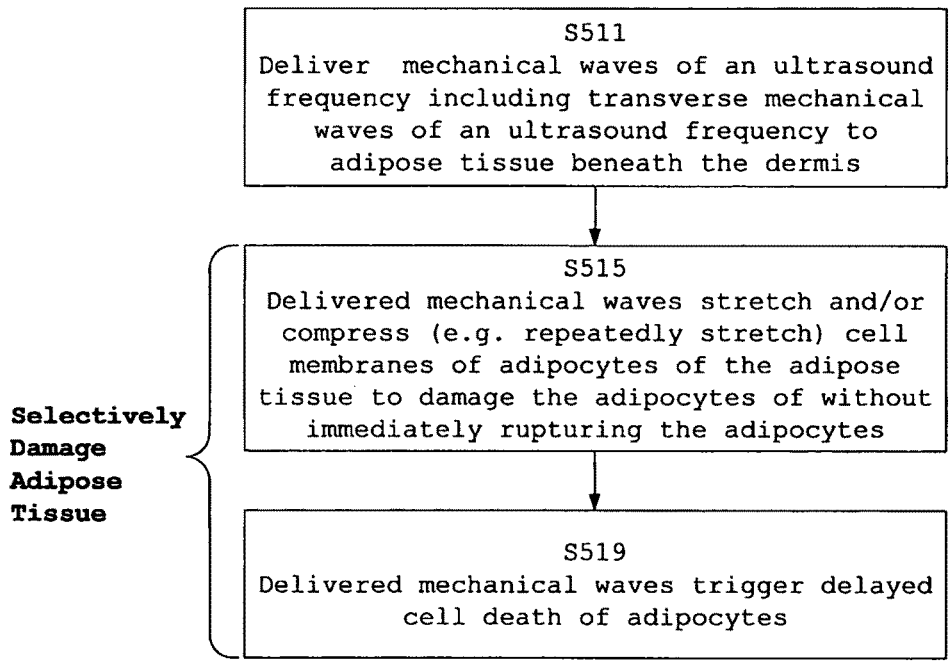
FIGS. 6A-6B are flowcharts of routines for selectively damaging adipose tissue.
Figure 6B:
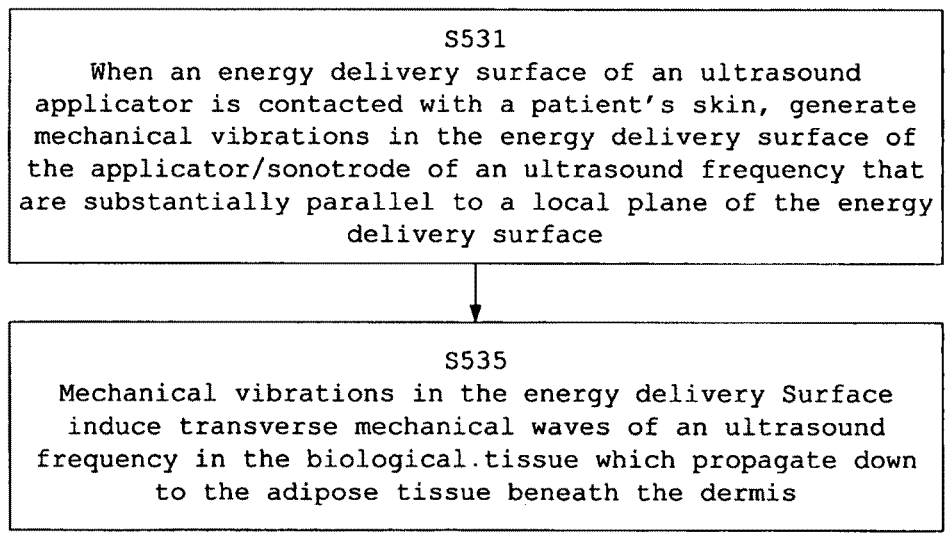

Discussion of FIGS. 6A-6B—A Flowchart of a Technique for Treating Adipose Tissue with Transverse Ultrasound Waves FIG. 6A is a flow chart of a technique for treating adipose tissue with transverse mechanical waves of ultrasound frequency. In step S511, the transverse mechanical waves of ultrasound frequency are delivered to adipose tissue beneath the dermis—for example, using a sonotrode 140 such as or similar to the sonotrode depicted in FIGS. 4, 7A-7B.

The mechanical waves of ultrasound frequency are delivered such that in step S515 the cell membranes of the adipocytes are repeatedly stretched to damage the adipocytes by deformation without immediately rupturing a most of the damaged adipocytes (for example, see FIG. 5A).

The mechanical waves of ultrasound frequency are delivered to trigger a biological process so that in step S519, "delayed death" of the adipocytes is triggered.

FIG. 6B is a flow chart of an exemplary implementation of step S511 according to some embodiments. In step S535, at a time that energy delivery surface 180 of sonotrode 140 is in contact with a patient's skin, the energy delivery surface mechanically vibrates in a direction that is substantially parallel to a local plane of energy delivery surface (for example, see FIGS. 9A-9C)

Figure 7B:
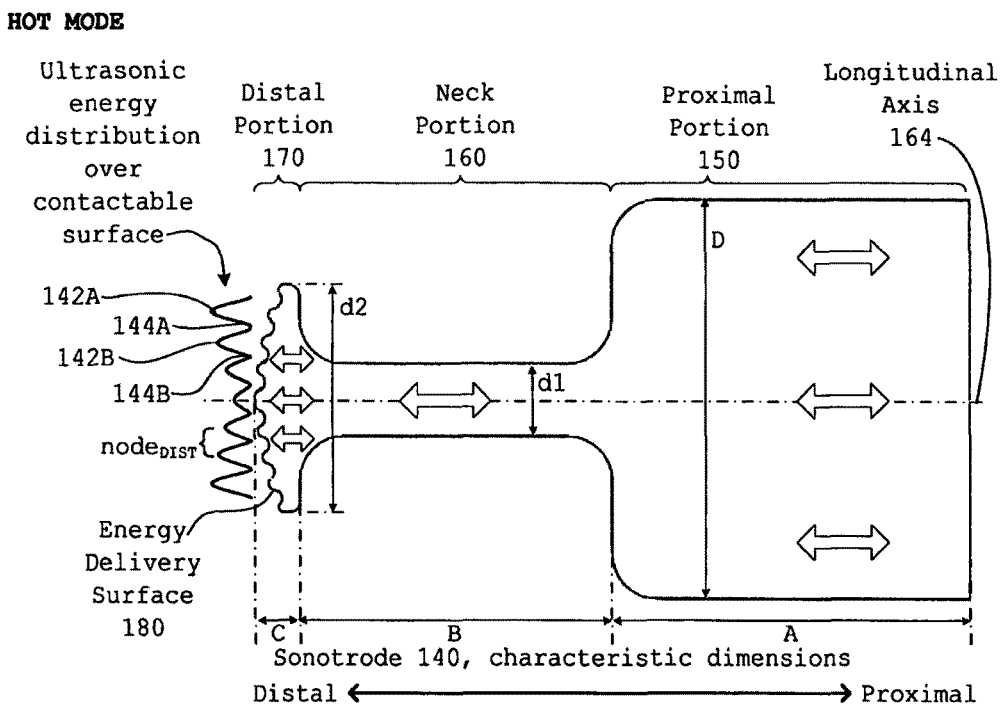
Figure 7C:
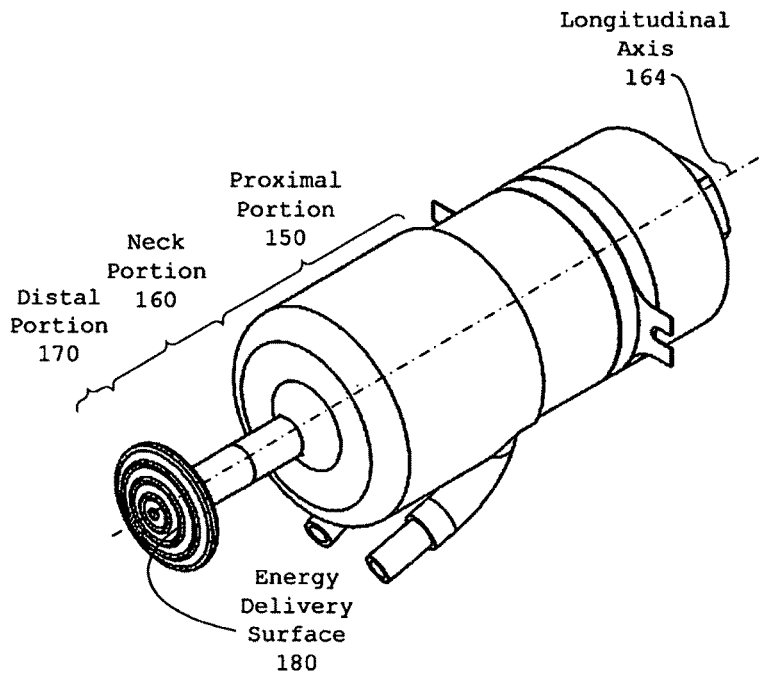

First Discussion of FIGS. 7A-7C—Sonotrode Dimensions and Ultrasound Wavelengths

FIG. 7A-7C are to-scale illustrations of "mushroom-shaped" ultrasound applicator or sonotrode 140.

It is stressed that the ratios between A, B, C, d1, D, R, d2 and all other feature of FIG. 7A are illustrative for the displayed embodiment only and are not to be construed as limiting in any way whatsoever.

In the non-limiting examples of FIG. 7A-7C, sonotrode 140 is symmetric about longitudinal axis 164, though this is not a limitation; a sonotrode according to the invention may be asymmetric about the longitudinal axis 164.

Sonotrode 140 includes: (i) proximal portion 150, (ii) distal portion 170 and (iii) an elongated neck portion 160 defining an elongated neck axis. In the non-limiting example of FIG. 7A, sonotrode 140 is substantially axisymmetric, so the elongate neck axis coincides with longitudinal axis 164, though this is not a limitation, Sonotrode 140 also includes or is operatively coupled to an ultrasound transducer 130. In the example of FIGS. 4 and 7A-7B, ultrasound transducer 130 may be attached to a proximal portion 150, although other configurations are contemplated (for example, where ultrasound transducer 130 is placed on a surface of proximal portion 150, such as the surface opposite the neck portion of the sonotrode).

As shown in FIG. 7A, sonotrode 140 is constructed, for example, as a solid and/or hollow form such that when ultrasound transducer 130 generates longitudinal mechanical waves of a particular driving ultrasound frequency within proximal portion 150, energy of these longitudinal waves travels into neck portion 160 and induces distal portion 170 to vibrate at an ultrasound frequency in a direction that is substantially perpendicular to the longitudinal direction of the sonotrode (i.e., a direction parallel to longitudinal axis 164). Thus, ultrasound transducer 130 may induce a standing wave in distal portion 170 in a direction that is substantially perpendicular (e.g., within a tolerance of 25, 20, 10, or 5 degrees) to longitudinal axis 164.

Thus, in FIG. 7A, sonotrode 140 is operative to "convert" plunger-type vibrations in proximal portion 150 and neck portion 160 into bending-type (or transverse) vibrations in distal portion 170.

In the non-limiting example of FIG. 7A, sonotrode 140 is dimensioned so that: (i) the ratio between dimension B of the neck portion 160 parallel to the elongate axis of the neck and dimension d1 of the neck portion 160 perpendicular to the elongate axis of the neck is at least 1.5 (or at least 2 or at least 2.5); (ii) the ratio between dimension d2 of the distal portion 170 perpendicular to the elongate axis of the neck and dimension C of the distal portion 170 parallel to the elongate axis of the neck is at least 2 (or at least 2.5 or at least 3); (iii) the ratio between dimension D of the proximal portion 150 perpendicular to the elongate axis of the neck and dimension d1 of the neck portion 160 perpendicular to the elongate axis of the neck is at least 2.5 (or at least 3 or at least 3.5); (iv) the ratio between dimension d2 of the distal portion 170 perpendicular to the elongate axis of the neck and dimension d1 of the neck portion 160 perpendicular to the elongate axis of the neck is at least 2 (or at least 2.5 or at least 3).

Although not a limitation, in studies conducted by the present inventors, it was determined that the oscillation mode illustrated in FIG. 7A whereby transverse vibrations are induced in distal portion 170 is obtainable when $d2 < \Lambda/4$, where Λ is the wavelength of bending (i.e., transverse) oscillation in the sonotrode material.

In one non-limiting example, the wavelength Λ of the mechanical wave of an ultrasound frequency may be as follows:

|  | Λ longitudinal (mm) | Λ transverse (mm) |
| --- | --- | --- |
| Aluminum | 105 | 43 |
| Stainless steel | 95 | 44 |
| Saline, salted water and lymph | 24 | — |
| Fibers (collagen) approx | 39 | 14 |

In FIG. 7A, the figure is labeled as "cold mode" because, in some embodiments, when the vibrations in the distal portion are substantially perpendicular to the longitudinal axis 164, mechanical energy that is primarily in the form of transverse mechanical waves of ultrasound frequency is delivered to the biological tissue in a manner that does not substantially heat the biological tissue.

In some embodiments, in order to achieve the "cold mode" effect described in FIG. 7A, transducer 130 needs to generate ultrasound at a special "driving frequency" or "resonant frequency."

In FIG. 7B, the ultrasound waves generated by transducer 130 are at driving frequency different from the cold mode driving frequency. In the example of FIG. 7B, instead of mechanical vibrations being induced in a direction substantially perpendicular to the elongate axis of neck 160 and to longitudinal axis 164 in the distal portion 170 "resonator," the vibrations are induced in a direction parallel to those axes. These vibrations are useful for delivering a longitudinal wave to biological tissue 200, thereby heating the biological tissue (thus FIG. 7B is labeled "hot mode"). When present, cavitation formation within the biological tissue may facilitate this heating.

Second Discussion of FIGS. 7A-7C—Cold Mode, Hot Mode and Wave Nodes

In some embodiments, when apparatus 100 is in "cold mode" or "transverse wave mode" (see FIG. 7A) then: (i) at least a minimum percentage (e.g., at least 30% or at least 50% or at least 70% or at least 90%) of ultrasound vibration energy within distal portion 170 is transverse ultrasound vibrations that are substantially perpendicular to the elongate axis of neck portion 160 and/or longitudinal axis 164; and/or (ii) at least a minimum percentage (i.e., at least 30% or at least 50% or at least 70% or at least 90%) of ultrasound wave energy delivered via energy delivery surface 180 are transverse ultrasound waves.

In some embodiments, when apparatus 100 is in "hot mode" or "longitudinal wave mode" (see FIG. 7B) then one or more of the following conditions are satisfied: (i) at least a minimum percentage (e.g., at least 30% or at least 50% or at least 70% or at least 90%) of ultrasound vibration energy within distal portion 170 is longitudinal ultrasound vibrations that are substantially parallel to an elongate axis of neck portion 160 and/or longitudinal axis 164; and (ii) at least a minimum percentage (e.g., at least 30% or at least 50% or at least 70% or at least 90%) of energy of ultrasound waves delivered via energy delivery surface 180 are longitudinal ultrasound waves.

One feature of FIG. 7A relates to the direction of ultrasound vibrations at transducer 130. It is noted that although the ultrasound vibrations within the distal portion 170 may be primarily vibrations in a direction substantially perpendicular to the elongate axis of neck portion 160 and/or substantially perpendicular to central longitudinal axis 164 (within a tolerance of 30 degrees or degrees or 10 degrees), the generated vibrations at transducer 130 (and/or within the proximal portion and/or within neck portion) are primarily (i.e., at least 50% but may also be at least 70% or at least 90% by energy) in a direction that is substantially parallel to an elongate axis of neck portion 160 and/or substantially parallel to longitudinal axis 164 (within a tolerance of 30 degrees or 20 degrees or 10 degrees.). Furthermore, in some embodiments, the generated vibrations at transducer 130 (and/or within proximal portion and/or neck portion) may be primarily (i.e., at least 50% but may also be at least 70% or at least 90% by energy) in a direction that is substantially perpendicular (within a tolerance of 30 degrees or 20 degrees or 10 degrees.) to a local plane of the skin in contact with energy delivery surface 180.

In the example of FIG. 7A, the ultrasound vibrations may be generated by an elongated transducer 130 whose elongate axis is substantially parallel (within a tolerance of 30 degrees or 20 degrees or 10 degrees) to a surface of the skin in contact with energy delivery surface 180. In some embodiments, the elongate axis of transducer 130 is substantially perpendicular (i.e., within a tolerance of 30 degrees or 20 degrees or 10 degrees) to an elongate axis of neck portion 160 and/or substantially perpendicular (i.e., within a tolerance of 30 degrees or 20 degrees or 10 degrees) to longitudinal axis 164.

As illustrated in FIGS. 7A-7B, ultrasound vibrations may be generated within sonotrode 140 so that a plurality of nodes 142 and anti-nodes 144 are produced. At the positions of the nodes 142 there may be a local maximum in ultrasound vibration intensity, and at the positions of the antinodes 144 there is a local minimum.

As shown in FIGS. 7A-7B, the distance between adjacent nodes or antinodes is $node_{DIST}$. It is noted that there is no requirement that $node_{DIST}$ remain the same in both modes—in fact, in many embodiments, $node_{DIST}$ is different for each mode.

In some embodiments, the distance between adjacent nodes or antinodes may depend on the prevailing mode—i.e. when in 'cold' mode where a majority of the ultrasound energy delivered from energy delivery surface 180 is energy of traverse ultrasound waves, $node_{DIST}$ adopts a first value $(node_{DIST})^{traverse}$, and when in 'hot' mode where a majority of the ultrasound energy delivered from energy delivery surface 180 is energy of longitudinal ultrasound waves, $node_{DIST}$ adopts a second value $(node_{DIST})^{longitudinal}$.

Third Discussion of FIGS. 7A-7C—Ultrasound Energy Intensity as a Function of Location on Energy Delivery Surface 180

As may be observed in FIGS. 7A-7B from the ultrasound energy distribution over contactable 'energy-delivery' surface 180, in some embodiments, the intensity of the ultrasound is greater at the "boundary" of energy-delivery surface, and lesser near the "center" (for example, where longitudinal axis 164 intersects energy delivery surface 180). Thus, in some embodiments, i) the sonotrode includes an energy delivery surface 180 for delivering energy of the induced ultrasound vibrations to the patient's skin; and ii) when the transducer 130 is in operation, the energy flux is at most 30% of the maximum energy flux on the energy on the energy delivery surface 180 at a point on the energy delivery surface 180 where the elongate axis of the neck intersects the energy delivery surface 180.

Figure 8:
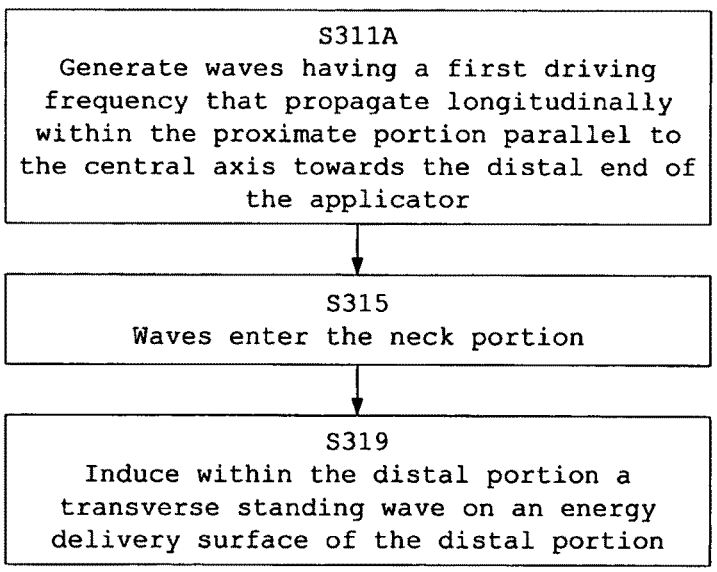
FIG. 8 is a flowchart of exemplary routines for generating transverse ultrasound waves within a mushroom-shaped ultrasound applicator/sonotrode while the ultrasound device is in 'cold mode.'

Discussion of FIG. 8: A Routine for Operating in Cold Mode

FIG. 8 is a flow chart of an exemplary routine for generating mechanical vibrations in the energy delivery surface 180 of the applicator/sonotrode 140 that are substantially parallel to a local plane of the energy delivery surface and/or substantially perpendicular to an elongate axis of neck portion 160 (which may coincide with longitudinal axis 164).

In step S311A, ultrasound waves having a first driving frequency (for example, a cold mode resonant frequency illustrated in FIG. 15A) are generated, for example, by ultrasound transducer 130. These ultrasound waves propagate downwards (i.e., in a direction towards the distal portion 170) and enter the neck portion 160 in step S315. In step S319, the longitudinal waves drive or induce within distal portion 170 a transverse standing wave on energy delivery surface 180. It is this transverse standing wave that, in turn, induces traveling transverse waves in biological tissue 200 during treatment.

Discussion of FIGS. 9A-9C: Pinching and Pulling Motion

Not intending to be bound by any particular theory, it is noted that FIG. 9A-9C describe one theoretical model of how sonotrode 140 behaves when in "cold mode."

FIG. 9A illustrates the standing transverse mechanical wave on the energy delivery surface. In the particular mushroom-shaped sonotrode 140 of FIGS. 7A-7C, there may not be transverse motion at the intersection location 166 where longitudinal axis 164 meets the energy delivery surface due to the axisymmetric geometry of sonotrode 140. Energy delivery surface 180 functions as a "vibrating skin surface" which is driven by the ultrasound vibrations generated by ultrasound transducer 130. In embodiments where the sonotrode is axially symmetric about longitudinal axis 164, intersection location 166 is at the center of the energy delivery surface.

Reference is now made to FIGS. 9B-9C.

At a first moment in time t0, there is a "pinching" transverse motion towards the intersection location 166. At a later moment in time t1, there is a "pulling" transverse motion away from intersection location 166 due to surface deformation. This repeats itself.

In the example of FIGS. 9A-9C, there is a single stationary point 166 in cold mode that does not vibrate in a transverse direction. In other examples, there may be multiple stationary points 166, depending on the vibration modes.

A Fourth Discussion of FIG. 7A—Net Momentum in a Plane Perpendicular to Elongate Axis of Neck 160 when in Cold Mode Reference is made once again to FIG. 7A.

Not wishing to be bound by any theory, it is noted that due to symmetry, in some embodiments, the "net momentum" of matter of sonotrode 140 and/or of distal portion 170 in a plane P that is perpendicular to an elongate axis of neck 160 may be substantially zero because of the 'pinching/pulling". Thus, although momentum at certain subsections in the plane P may be non-zero, the net-momentum of matter within plane P of matter of sonotrode 140 at a time of transverse ultrasound vibrations may, nevertheless, be substantially zero due to these cancellation effects.

Thus, in some embodiments, it is possible to write (i.e. even in "cold mode" or "transverse wave mode")

$$\int_{SONOTRODE} \rho v_P \, dV \approx 0$$

or $$\int_{DISTAL\_PORTION} \rho v_P \, dV \approx 0,$$

where: (i) $\rho$ is the local density of matter of sonotrode 140; (ii) $v_p$ is the component of local velocity (i.e. on a microscopic scale due to ultrasound vibrations) within plane P that is perpendicular to an elongate axis of neck 160 or to longitudinal axis 164 of matter of sonotrode 140 at a given location within the sonotrode and; (iii) $dV$ is a differential volume element.

This may be normalized, and it may be possible, in some embodiments, to write:

$$\frac{\left[\int_{SONOTRODE} \rho v_P \, dV\right]^2}{\int_{SONOTRODE} \rho \, dV \times \int_{SONOTRODE} \rho (v_P)^2 \, dV} < \text{fraction,}$$

or $$\frac{\left[\int_{DISTAL\_PORTION} \rho v_P \, dV\right]^2}{\int_{DISTAL\_PORTION} \rho \, dV \times \int_{DISTAL\_PORTION} \rho (v_P)^2 \, dV} < \text{fraction.}$$

In different embodiments, the fraction may be equal to 0.3 or 0.2 or 0.1 or 0.05 or 0.01 or 0.005.

In the above, it is possible to define as follows:

$$\int_{SONOTRODE} \rho v_P \, dV \qquad (i)$$

as the total momentum in the plane P due to ultrasound vibrations of matter of sonotrode 140 when in "cold mode" or "transverse wave mode";

$$\int_{DISTAL\_PORTION} \rho v_P \, dV \qquad (ii)$$

as the total momentum in the plane P due to ultrasound vibrations of matter within distal portion 170 when in "cold mode" or "transverse wave mode";

$$\int_{SONOTRODE} \rho (v_P)^2 \, dV \qquad (iii)$$

as twice the total kinetic energy of matter of the sonotrode due to motion (i.e. of ultrasound vibrations) in plane P;

$$\int_{DISTAL\_PORTION} \rho (v_P)^2 \, dV \qquad (iv)$$

as twice the total kinetic energy of matter of the distal portion 170 due to motion (i.e. of ultrasound vibrations) in plane P;

$$\int_{SONOTRODE} \rho \, dV \qquad (v)$$

as the total mass of sonotrode 140;

$$\int_{DISTAL\_PORTION} \rho \, dV \qquad (vi)$$

as the total mass of distal portion 170.

In some embodiments, any of these conditions above (i.e. where the square of an integral appears in the numerator and the product of two integrals appears in the denominator) may prevail for at least 1 second or at least 3 seconds or at least 5 seconds.

A Discussion of FIGS. 10-13C—Treatment of a Plurality of Adipocytes

FIG. 10 illustrates a plurality of adipocytes 240 within a control volume 280. In some embodiments, it is recognized that there may be many adipocytes within control volume 280 (for example, at least 10,000 or at least 30,000 or at least 50,000 or at least 70,000 adipocytes within 1 cm^3), and not every single adipocyte will be sufficiently damaged to trigger delayed death.

As such, certain techniques are now disclosed to increase the success rate or fraction of cells within a large sample (e.g., a sample containing at least 10,000 adipocytes or at least 30,000 or at least 50,000 or at least 70,000 adipocytes within 1 cm^3) that are sufficiently damaged to trigger delayed adipocyte death. As shown in FIG. 10, this sample will be in control volume 280 (for example, a rectangular prism whose length, width, and depth are at least 1 cm, and which is "buried" beneath the dermis (e.g., at least 1 cm beneath the surface) so the distance between the nearest surface of the control volume 280 and the outer skin surface, d, is greater than or equal to 1 cm).

Thus, in some embodiments, the mechanical waves of an ultrasound frequency are delivered in a manner so as to (i) trigger delayed cell death within 3 days of a majority of adipocytes (or a substantial majority of at least 70% or at least 90%) residing within a rectangular prism control volume 280 of adipose tissue beneath the dermis (ii) without rupturing, within 30 minutes, any more than 2% (or any more than 5% or any more than 10% or any more than 20%) adipocytes 240 residing within the control volume 280. Control volume 280 of adipose tissue: (i) has a given thickness, length and width; (ii) has a given volume V equal to the product of the thickness, length and width (units of V are cubic centimeters); (iii) is located beneath the skin dermis; and (iv) includes at least a number X adipocytes, where X is the product of the volume V of control volume 280 in cubic centimeters and a number of adipocytes per cm^3 which is at least 10,000 cells or at least 30,000 cells or at least 50,000 cells.

In different examples, the size of V may be 1 cm$^3$, or 2 cm$^3$, or 4 cm$^3$ or 10 cm$^3$.

In one particular example, the thickness of control volume 280 is 1 cm, and the length and width are each 2 cm.

Reference is now made to FIG. 11A which illustrates damage to an adipocyte membrane 244 by an incident transverse mechanical wave of ultrasound frequency having a propagation axis that is labeled as 270. As shown in FIG. 11A, the extent of damage caused by the transverse mechanical wave of ultrasound frequency may depend upon an "orientation" of a non-spherical adipocyte relative to a propagation axis 270 of an incoming transverse mechanical wave.

The illustrative example of FIG. 11A relates to adipocytes 240 that are substantially shaped as prolate spheroids having a longitudinal axis 242, though it is appreciated that the adipocytes 240 may have other shapes including oblate spheroids, or non-spheroid shapes.

As illustrated in FIG. 11A, in the situation of "Case A," the incoming transversal mechanical wave is likely to inflict a greater amount of damage (due to stretching and/or compression of adipocyte membrane 240 in the direction of the two-headed block arrow) than in the situation of "Case B."

Thus, in some embodiments, a cell membrane 244 of a given adipocyte 240 is subjected to the most damage/injury if the orientation of the adipocyte 240 relative to the propagation axis 270 is such that an "elongated" surface of the cell membrane 244 is substantially perpendicular to the propagation axis 270 of the transverse wave.

Reference is now made to FIG. 11B. FIG. 11B shows (see 292) that in many clinical situations the adipocytes are not aligned but rather adopt many different orientations (see 294).

It is now disclosed that in order to achieve a more successful treatment of adipocytes with transverse mechanical waves, it may therefore be useful to deliver transverse mechanical waves with many different propagation axis 270 orientations (i.e., "scatter" the waves) rather than (a) delivering mechanical waves in substantially a single direction so that all propagation axes 270 of transverse mechanical waves delivered at a given time are substantially parallel to each other, or (b) focusing the waves.

Scattering the transverse waves may be useful for maximizing the likelihood that a given adipocyte receives a transverse mechanical wave from substantially the "correct" angle best-suited to inflict maximal damage to the cell membrane. Because the "correct" angle may be one of many different angles, the chance of achieving this correct angle increases if mechanical waves are delivered at a given time so that propagation axes are at various orientations.

One exemplary technique for accomplishing this is illustrated in FIG. 13A. By using a sonotrode having a convex rather than a flat surface, it is possible to scatter the delivered transverse mechanical waves to a certain extent into biological tissue 200.

As illustrated in FIG. 13A, it may be useful to employ an energy delivery surface 180 that includes a plurality of discontinuous surfaces and/or a plurality of protrusions (see for example, concentric circular ridges 182). This may be useful for facilitating scattering of the transverse mechanical waves into the tissue (for example, compare FIG. 12 with FIG. 13A).

Propagation Axes Distribution Function

As noted earlier, in some embodiments it may therefore be useful to deliver transverse mechanical waves with many different propagation axis 270 orientations rather than delivering mechanical waves substantially in a single direction. FIG. 13B illustrates a distribution of propagation axes of transverse mechanical waves delivered at a given time.

Reference is now made to FIG. 13C. In some embodiments, energy of mechanical transverse waves of ultrasound frequency is delivered from the energy delivery surface 180 such that, at a given time:

(i) at least a certain fraction f1 (for example, at least 30%) of energy is energy of transverse mechanical waves having a propagation axis 270 within an angle theta of a given direction 266 (in the example of FIG. 13C direction 266 is substantially parallel (i.e., within a 10, 20, or 30 degree tolerance) to elongate axis of neck portion 160 and/or to longitudinal axis 164 in "region 1"; and (ii) at least a certain fraction f2 (for example, at least 30%) of energy is energy of transverse mechanical waves having a propagation axis 270 that differs from the given direction 266 by more than the angle theta (i.e., in "region 2").

In one non-limiting example, theta=30 degrees.

A Discussion of FIG. 14—Wave Penetration

As shown in FIG. 14, the penetration depth (i.e., the depth beneath the skin surface at which the intensity of the delivered wave is reduced by a factor of e (approximately 2.718)) of the transverse wave is greater than the penetration depth of the longitudinal wave. The penetration depth of the transverse ultrasound waves (for the same energy) may be, for example, at least a factor of or 3 greater than that of longitudinal waves during implementation of the invention. In one non-limiting example where the frequency of the longitudinal wave mode is 61 kHz, this penetration depth is 5-10 mm for the longitudinal wave and 20-40 mm for the transverse mechanical wave.

It is understandable that absorption of the longitudinal wave is much higher because of cavitation in liquids within the biological tissue.

In some embodiments, the penetration depth of the longitudinal ultrasound wave is less than 1 cm, and the penetration depth of the transverse ultrasound wave is between 2 cm and 5 cm.

It is also evident from FIG. 14 that the intensity of the longitudinal wave at the skin surface may exceed the intensity of the transverse ultrasound wave (though FIG. 14 is not necessarily intended to be to-scale).

It is noted that when ultrasound energy (i.e., either longitudinal or transverse mechanical waves of ultrasound frequency) is delivered from energy delivery surface 180 to biological tissue 200, a first fraction of the mechanical energy delivered from energy delivery surface 180 is reflected back from the surface of biological tissue 200 and a second fraction of the mechanical energy delivered from energy delivery surface 180 is actually transmitted into biological tissue 200.

As discussed earlier, in some embodiments, impedance matching techniques (for example, applying petroleum jelly to energy delivery surface 180) are employed to maximize the second fraction (i.e. the fraction that is actually transmitted into the tissue).

Not intending to be bound by any particular theory, in some embodiments, the transverse wave is not refracted as much as the longitudinal wave. This occurs because transverse waves travel slower than longitudinal waves. Therefore, the velocity difference between the incident wave and refracted transverse wave is not as great, as it is between the incident and refracted longitudinal waves. Therefore, the shear wave can penetrate "deeper" because of lower refractions.

In one non-limiting example, (i) 40-80 watts of mechanical waves of ultrasound frequency are delivered from energy delivery surface 180 ("input" power from the sonotrode 140); (ii) when in "hot" mode, 50% of the input power is absorbed by the tissue 200, while the other 50% is reflected back from the skin surface); (iii) when in "cold" mode, only 25% of the input power is absorbed by the tissue 200 while 75% of the input power is reflected.

Although only a relatively small fraction of transverse mechanical wave energy is absorbed in this non-limiting example (thereby providing only weak mechanical waves in the tissue 200), it is noted that in some embodiments this is sufficient to provide effective fat treatment because there is no requirement to rupture adipocytes, only to "gently" damage (or deform) the adipocytes to trigger delayed cell death of adipocytes.

Figure 15B:
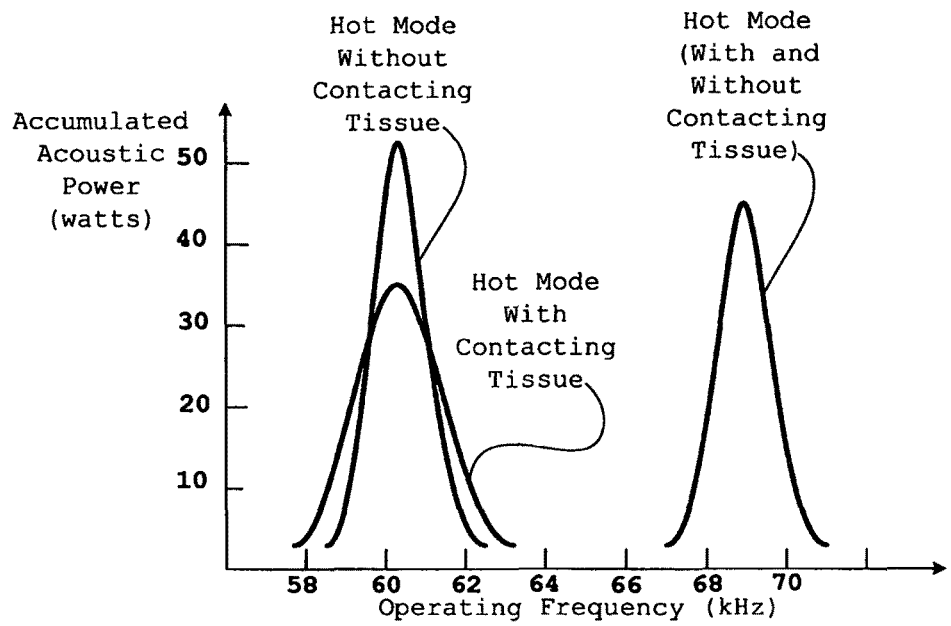

A Discussion of FIG. 15A-15B—Multiple Resonant Frequencies of Sonotrode 140

As shown in FIG. 15A-15B, sonotrode 140 may be characterized by multiple resonant frequencies. Thus, for the example case of FIG. 15A, there are two resonant frequencies: a "cold mode" resonant frequency of about 69 kHz, and a "hot mode" resonant frequency of about 60 kHz. When ultrasound transducer 130 generates ultrasound at the first driving or resonant frequency of 69 kHz, sonotrode 140 adopts the first mode (i.e. cold mode) described in FIGS. 7A, 8, 9A-9C and 17A, where the vibrations in the distal portion 170 resonator are primarily in a direction substantially perpendicular to elongate neck axis (which happens to coincide with longitudinal axis 164) and where a transverse mechanical standing wave is generated in distal portion 170.

When ultrasound transducer 130 generates ultrasound at the second driving or resonant frequency of 69 kHz, sonotrode 140 adopts the second mode (i.e., the hot mode) described in FIGS. 7B, 16 and 17B, where the vibrations in the distal portion 170 resonator are primarily in a direction substantially parallel to elongate neck axis (which happens to coincide with longitudinal axis 164) and where a longitudinal mechanical standing wave is generated in distal portion 170.

It will be appreciated that resonant frequency values depicted in FIG. 15A are illustrative only and may be appropriate for the system of FIGS. 7A-7C where the applicator is constructed of aluminum. In other situations, the values may differ from those depicted in FIG. 15A. Furthermore, it will be appreciated that there is no requirement of only a single cold mode resonant frequency and only a single hot mode resonant frequency as depicted in FIG. 15A. Indeed, in some embodiments, there are multiple hot and/or cold resonant frequencies (not shown in the figure).

FIG. 15B illustrates, for the same example depicted in FIG. 15A, the effect of the biological tissue load upon the Q-factor of the sonotrode 140 "resonator." As is evident in FIG. 15B, cold mode curve is practically independent of load (human tissue) coupling and is substantially the same with and without the load. The hot mode provides quite different results—i.e. the lower curve is when the biological load is contacted to sonotrode 140 and the higher curve is when no biological load is in contact with sonotrode 140. It is thus clear that the contacting decreases the Q-factor of the resonator because of energy losses to the biological tissue.

A Discussion of FIG. 16—A Routine for Operating in Hot Mode

FIG. 16 is a flow chart of an exemplary routine for operating sonotrode 140 in hot mode.

In step S311B, ultrasound waves having a second driving frequency (for example, a hot mode resonant frequency illustrated in FIG. 12—this "second" driving frequency is in contrast with the "first" driving frequency of step S311A of FIG. 8) are generated, by ultrasound transducer 130. These ultrasound waves propagate downwards in the direction of the distal portion of the sonotrode and enter the neck portion 160 in step S315. In step S319, the longitudinal waves drive or induce within distal portion 170 a longitudinal standing wave on energy delivery surface 180. It is this longitudinal standing wave of the surface that, in turn, induces longitudinal waves in biological tissue 200 during treatment.

Path of High Frequency ("HF") and Ultrasonic Energy Flow

In some embodiments, the path of HF and ultrasonic energy is as follows (in consecutive order): (i) HF-generator; (ii) ultrasound transducer 130; (iii) proximal portion 150 of sonotrode 140; (iv) neck portion 150 of sonotrode 140; (v) distal portion 170 of sonotrode 140; (vi) contactable energy delivery surface 180 of distal portion 170; (vii) acoustic impedance matching material between distal portion 170 and an upper surface (i.e., a skin surface) of biological tissue 200 (e.g., plastic, Teflon®, petroleum jelly, or the like); (viii) epidermis 210; (ix) dermis 220; (x) subcutaneous layers 230; (xia) adipocyte cell membranes 244 of adipocytes 240 of the adipose tissue 230 for transverse mechanical waves; or (xib) liquid content of adipocytes (e.g., semi-liquid triglycerides) for longitudinal mechanical waves.

A Discussion of FIG. 17A—A Routine for Operating in Cold Mode

FIG. 17A is a flow chart of an exemplary technique for operating ultrasound apparatus 100 including sonotrode 140 in cold mode.

In step S511, high frequency electrical current is generated by current source 110. In step S515, energy of the electrical current is converted (for example, by ultrasound transducer 130) to ultrasound energy—for example, ultrasound energy whose frequency matches the driving frequency of the cold mode (in the example of FIG. 12, about 69 kHz). In step S519, ultrasound waves propagate within sonotrode 140 (for example, in a longitudinal direction in proximal 150 and neck 160 portions towards distal portion 170) and induce vibrations of the distal portion 170 resonator. In step S523, standing transverse mechanical waves of an ultrasound frequency resonate in a direction substantially perpendicular to an elongate axis of neck portion 160 and to the longitudinal axis 164 causing the delivery of transverse mechanical waves of ultrasound frequency from energy delivery surface 180.

In step S527, the transverse mechanical waves propagate through an impedance matching material (e.g., petroleum jelly). In step S531, this transverse mechanical wave propagates through the dermis and epidermis layers to reach the subcutaneous layers. In step S535, the transverse mechanical wave propagates through the adipose tissue beneath the dermis. In particular, the transverse mechanical wave propagates through fibers and/or cell membranes to damage, injure, and/or deform the cell membranes, which ultimately triggers a biological process of delayed cell death.

A Discussion of FIG. 17B—A Routine for Operating in Hot Mode

FIG. 17B is a flow chart of an exemplary technique for operating ultrasound apparatus 100 including sonotrode 140 in hot mode.

In step S411, high frequency electrical current is generated by current source 110. In step S415, energy of the electrical current is converted (for example, by ultrasound transducer 130) to ultrasound energy—for example, ultrasound energy whose frequency matches the driving frequency of the hot mode (in the example of FIG. 12, about 59 kHz). In step S419, ultrasound waves propagate within sonotrode 140 (for example, in a longitudinal direction in proximal 150 and neck 160 portions towards distal portion 170) and induce vibrations of the distal portion 170 resonator. In step S423, standing transverse mechanical waves of an ultrasound frequency resonate in a direction substantially parallel to an elongate axis of neck portion 160 and to the longitudinal axis 164 causing the delivery of longitudinal mechanical waves of an ultrasound frequency from energy delivery surface 180.

In step S427, the transverse mechanical waves propagates through an impedance matching material (e.g., petroleum jelly). In step S531, this longitudinal mechanical wave propagates through the dermis and epidermis layers to reach the subcutaneous layers. In step S435, the longitudinal wave propagates through adipose tissue beneath the dermis. In particular, the longitudinal mechanical wave may propagate through a liquid fraction (e.g., semi-liquid triglycerides) of adipocytes to heat the adipose tissue. In some embodiments, the dermis and/or epidermis are also heated by the longitudinal ultrasound waves.

A Discussion of FIGS. 18 and 19—Hybrid Treatment Routines

In some embodiments, it may be useful to pre-heat upper layers of the biological tissue before delivering the transverse mechanical waves of ultrasound frequency. This may be useful for improving the acoustic conductivity of upper layers of tissue for mechanical waves of ultrasound frequency, allowing deeper and/or more efficient penetration of the transverse waves into the biological tissue, or to allow a greater fraction of the energy to penetrate to a given depth in the tissue.

In one embodiment, this is accomplished by operating ultrasound apparatus 100 in "hot mode" (see FIG. 18). Alternatively or additionally, another form of energy may be provided to heat upper layers of tissue (for example, RF energy—see FIG. 19).

FIG. 18 is a flow chart of a cyclical hybrid treatment technique provided in accordance with some embodiments.

In step S201 sonotrode 140 is brought into contact (or proximity) with the skin surface. Although step S201 is depicted as occurring before step S205, this is not a limitation, and other orders are contemplated and may be used.

In step S205, a preliminary or first treatment stage is carried out wherein longitudinal ultrasound energy is delivered via energy delivery surface 180 to heat the biological tissue for a period of time $t_{hot}$ (e.g., between 2 and 10 seconds, or between 4 and 6 seconds). Thus, in some embodiments, the mechanical wave energy of an ultrasound frequency delivered during step S205 is primarily longitudinal wave energy (i.e., at least 50%, 70%, or 90% longitudinal mechanical wave energy).

In some embodiments, step 205 is operative to heat a 'control' region of the dermis and/or of the epidermis (for example, having a thickness of at least 0.5 cm and an area of at least 5 cm^2 for a total volume of 2.5 cm^3) to a temperature that is at least about 42 degrees Celsius (or at least 45 degrees) for a period of time that is at least about 2 seconds, or at least 4 seconds or at least 8 seconds.

Optionally, epidermal cooling is used during the hot mode pre-heating phase of step S205 and/or main phase of step S209, in order to reduce pain and to prevent sonotrode 140 from "overheating" (for example, heating above 50 degrees Celsius or 60 degrees Celsius or 70 degrees Celsius or any other 'undesirable' temperature). Any technique for cooling a sonotrode known in the art may be used—for example, cooling with a liquid such as water.

In some embodiments, for a majority of the time of step S205 (for example, at least 50% or at least 70% or at least 90% of the time), the power flux of the delivered longitudinal ultrasound wave energy which is delivered from applicator 140 is at least about 3, 5, 7, or 10 watts/cm^2.

In some embodiments, this power flux it at most about 35, 25, or 20 watts/cm^2.

In some embodiments, for a majority of the time of step S205 (for example, at least 50% or at least 70% or at least 90% of the time $t_{HOT}$ step S205), the delivered ultrasound waves comprise, at least 90% (or at least 70% or at least 50%) longitudinal ultrasound waves.

In step S209, a main treatment phase is carried out wherein mechanical waves of ultrasound frequency are delivered to the biological tissue 200 via energy delivery surface 180 for a period of time $t_{COLD}$ (e.g., between 10 and 30 seconds, or between 15 and 25 seconds). At least about 30%, 50%, 70%, or 90% of the energy of the mechanical waves of ultrasound frequency are transverse wave energy for at least 90% or at least 70% or at least 50% of the time $t_{COLD}$ of step S209.

In some embodiments, a power level of delivered mechanical waves of an ultrasound frequency (i.e. delivered to the biological tissue via energy delivery surface 180) during step S209 is at least 20% or at least 30% or at least 50% a power level of delivered mechanical waves of an ultrasound frequency (i.e. delivered to the biological tissue via energy delivery surface 180) during step S205.

In some embodiments, during the cold mode at least a portion of the dermis (for example, having a thickness of at least 0.5 cm and an area of at least 5 cm^2 for a total volume of 2.5 cm^3) is allowed to cool by at least about 1 or 2 degrees Celsius as transverse mechanical wave energy is delivered to biological tissue 200.

In some embodiments, the power flux of the delivered transverse ultrasound wave energy which is delivered from applicator 140 during the step S205 is at least about 3, 5, 7, or 10 watts/cm$^2$.

In some embodiments, this power flux it at most 35 watts/cm$^2$ or at most 25 watts/cm$^2$ or at most 20 watts/cm$^2$.

Although these power fluxes have been explained in the context of FIG. 18, it is appreciated that these power fluxes may be employed in any embodiment and are not limited to embodiments of FIG. 18.

Thus, in some embodiments, a ratio of the average power flux during step S205 and step S209 is at least about 0.3, 0.5, 0.7, or 0.9.

Thus, in some embodiments, a ratio of the average power flux during step S205 and step S209 is at most about 3, 2, or 1.5.

In one particular example, the average power flux delivered from sonotrode 140 during step S205 is substantially equal (i.e., within a tolerance of, for example, about 50%, 30%, 10%, 5%, or 1%) to the average power flux delivered from sonotrode 140 during step S209. Nevertheless, because the longitudinal energy of step S205 is better absorbed than the transverse energy of step S209 for which a greater fraction is reflected from biological tissue, in these embodiments, more energy may be absorbed by biological tissue 200 during step S205.

As illustrated in FIG. 18, steps S205 and S209 may be repeated any number of times in order, such as, for example, at least about 5 times or 10 times.

In some embodiments, the ratio between $t_{COLD}$ and $t_{HOT}$ is at least 2:1 or at least 2.5:1. In some embodiments, the ratio between $t_{COLD}$ and $t_{HOT}$ is at most 5:1 or at most 3.5:1.

In one preferred embodiment, the ratio between $t_{COLD}$ and $t_{HOT}$ is about 3:1.

In one experiment conducted by the present inventors, the following parameters were employed: (i) a total of 30 treatment cycles were delivered within 10 minute treatment time; (ii) for each treatment cycle, $t_{HOT}$=5 seconds and $t_{COLD}$=15 seconds, providing a 3:1 ratio between the durations of step S209 and step S205; (iii) for each treatment cycle, the fraction of mechanical wave energy of an ultrasound frequency that was longitudinal wave energy during step S205 was at least 90% and the fraction of mechanical wave energy of an ultrasound frequency that was transverse wave energy during step S207 was at least 90%.

As noted above, in some embodiments, mechanical waves of ultrasound frequency are delivered from sonotrode 140 at during the time that sonotrode 140 is in transverse motion over, the surface of the biological tissue.

In some embodiments, the recommended total treatment time for all cycles is between about 0.25 min/cm$^2$ and 0.45 min/cm$^2$ of tissue treated.

In one example, 100 cm$^2$ is treated, and the minimum recommended time of treatment is 25 minutes, and the maximum recommended time of treatment is 45 minutes. In the event that each treatment cycle is 20 seconds (e.g., 5 seconds of cold mode and 15 seconds of hot mode), between 75 and 135 treatment cycles is preferred.

It is appreciated that in different clinical conditions the number of cycles and/or the ratio between $t_{COLD}$ and $t_{HOT}$ may differ from the values reported in this section.

It is noted that, in some embodiments, the cold mode of step S209 is provided by causing transducer 130 to operate at a first "driving frequency" associated with the "cold mode" resonant frequency (see FIGS. 15A-15B), and the hot mode of step S205 is provided by causing transducer 130 to operate at a second "driving frequency" associated with the "hot mode" resonant frequency.

In one embodiment, a difference between the first and second driving frequencies is at least 3 kHz.

In one embodiment, a ratio between (i) the difference between the first and second driving frequencies; and (ii) a maximum of the first and second driving frequencies is at least 0.1.

In one embodiment, the device controller 120 is operative to cause the sonotrode 140 and the ultrasound transducer 130 to: A) effect (i.e., in step S205) a preliminary phase of a duration having a duration $t_{HOT}$ that is at least 10 seconds and at most 30 seconds where the sonotrode 140 and the ultrasound transducer 130 provide the longitudinal wave mode; and B) after the preliminary phase, effect (i.e., in step S209) a main phase having a duration $t_{COLD}$ that is at least twice the duration $t_{HOT}$ of the preliminary phase where the sonotrode 140 and the ultrasound transducer 130 provide the transverse wave mode.

In some embodiments, the controller 120 is operative to repeat the preliminary and the main phases at least 10 times.

In some embodiments, the controller 120 is operative to commence the main phase of step S209 within 15 seconds of a completion of the preliminary phase of step S205.

In some embodiments, the controller 120 is operative such that a ratio between the duration $t_{COLD}$ of the main phase and the duration $t_{HOT}$ of the preliminary phase is at most 5.

As indicated in FIG. 19, it is possible to provide preheating using techniques other than ultrasound-based techniques. In one example, RF energy is delivered to the biological tissue 200 to pre-heat the biological tissue during the preliminary phase.

Figure 20:
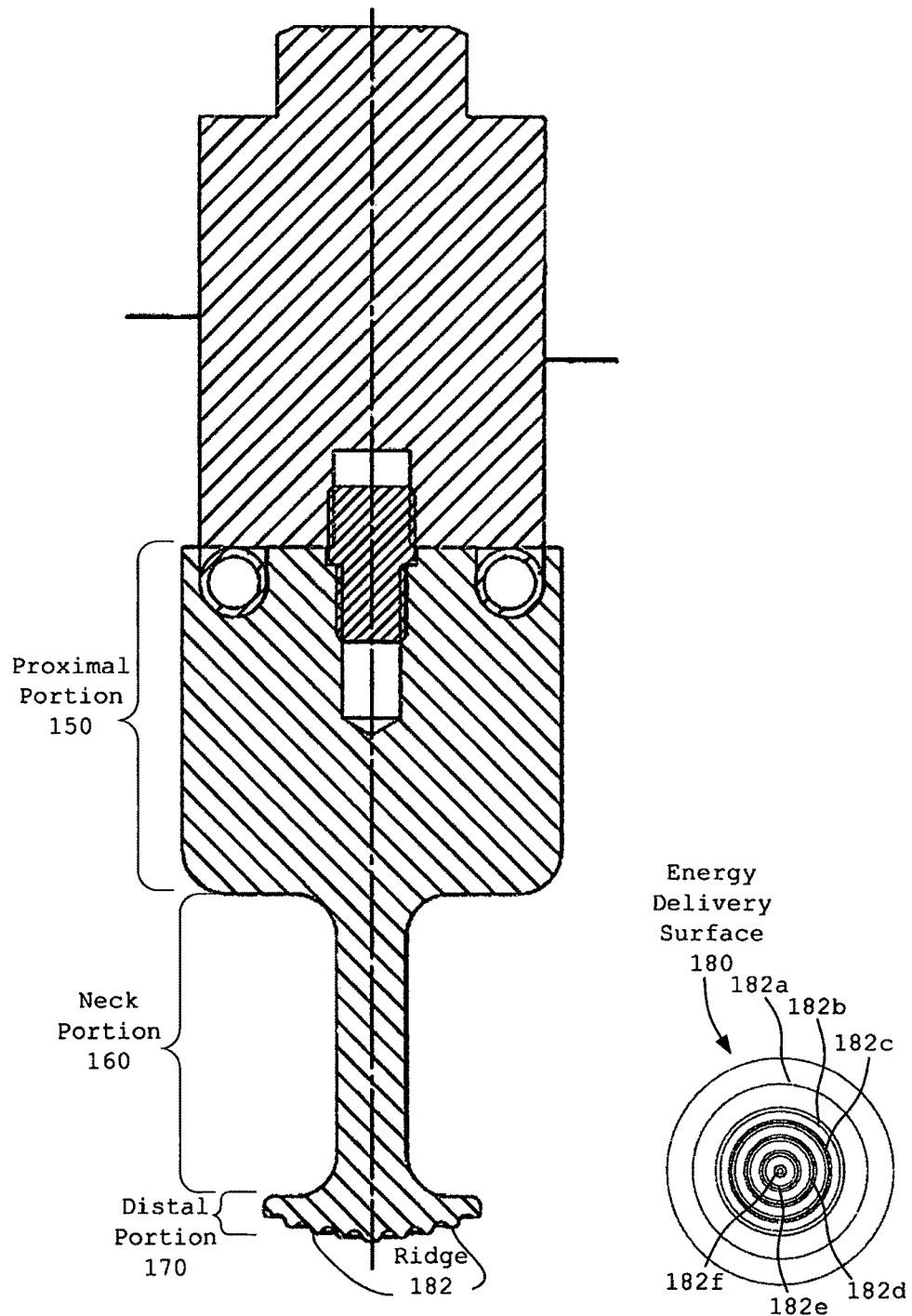
FIGS. 20A-20B are illustrations of an energy-delivery surface including a plurality of ridges or protrusions.

A Discussion of FIGS. 20A-20B—Additional Discussion about the Structure of Sonotrode 140

FIG. 20A is a cross-section image of sonotrode 140 including a plurality of protrusions or ridges 182

FIG. 20B illustrates the concentric ridges 182 located on energy delivery surface 180. As shown in FIG. 20B, the ridges are "denser" towards the center of energy delivery surface. Also, it is noted that in some embodiments, the positions of the concentric ridges 182 may coincide with the position of the nodes or anti-nodes of the ultrasound waves delivered via energy delivery surface (i.e. either longitudinal or transverse ultrasound waves).

Thus, in some embodiments, a distance between adjacent concentric ridges 182 may be an integral multiple (or a reciprocal of an integral multiple) of node$_{DIST}$ a distance between adjacent nodes or anti-nodes (FIGS. 7A-B), in either the "hot mode" or the "cold mode" (i.e., a multiple of (node$_{DIST}$)$^{traverse}$ and/or (node$_{DIST}$)$^{longitudinal}$).

Figure 21:
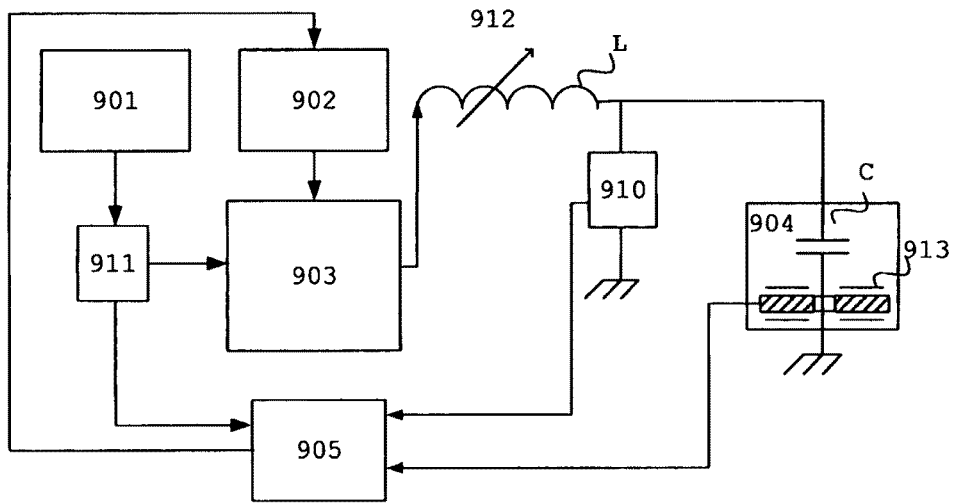
FIG. 21 illustrates electric circuitry of an ultrasound device in accordance with some embodiments.

A Discussion of FIG. 21—Electric Circuitry for Supplying Current to Transducer 130

FIG. 21 illustrates electric circuitry for supplying a regulated electrical current to ultrasound transducer 130. The electrical circuitry of FIG. 21 may include the following elements: 904—internal capacitance of the ultrasonic transducer; 912—resonant RF-inductor (which together with element 904 comprises the in-series resonance circuit); 903—HF-generator supplying transducer 904, for example, the generator may be an E-class switching module based on the Mosfet transistor; 901—DC-power supply; 911—DC-current sensor (serving for DC-current resonance control; 910—HF-voltage sensor (serving for control of resonance at LC-circuit (912/904); 913—ultrasonic energy sensors; 905—system controller (microprocessor based); 902—HF-driver of the generator 903.

Figure 22:
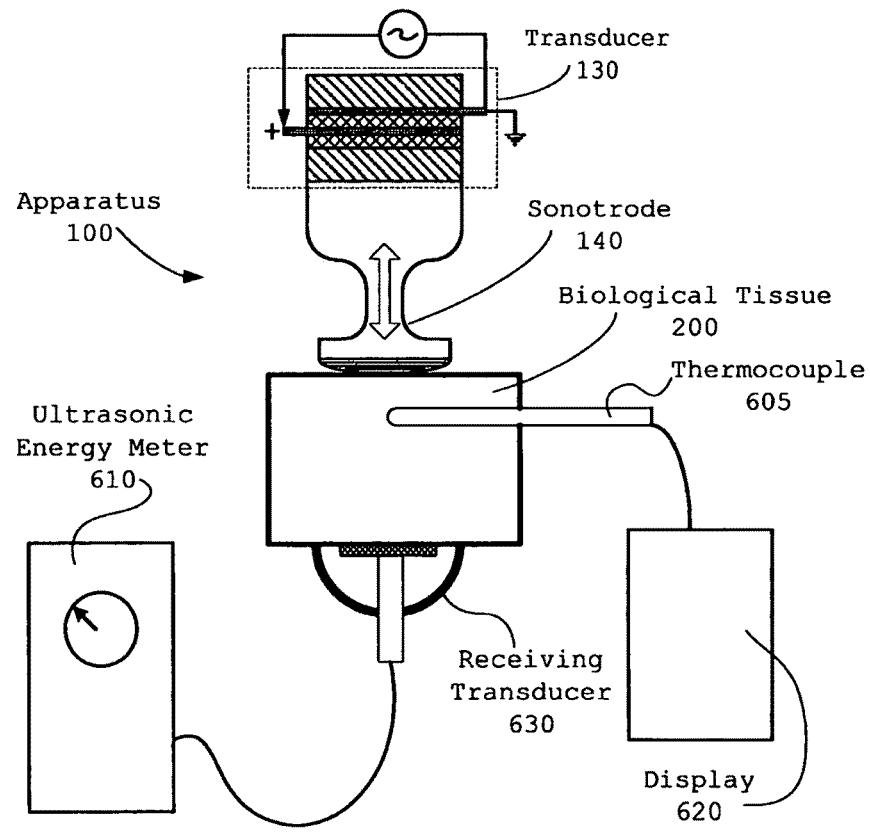
FIG. 22 illustrates a system for calibrating a multi-mode ultrasound device.
Figure 23:
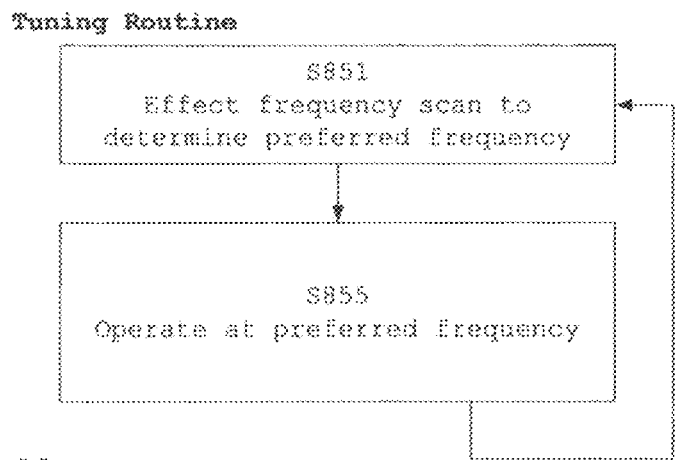
FIG. 23 is a flow chart of a routine for frequency scanning.

A Discussion of Resonance Tuning (FIGS. 22-23)

FIG. 22 is an illustration of a system for determining 'hot mode' and 'cold mode' 'driving' resonant frequencies for "calibration" of apparatus 100. The system of FIG. 22 includes biological tissue (for example, pig flesh) to which ultrasound energy is delivered.

When the apparatus 100 is in "hot mode" then the temperature of the biological tissue is relatively "hot" and this is detected by thermocouple 605 which is operatively linked to display 620.

When the apparatus 100 is in "hot mode" most of the energy is dissipated at relatively "shallow depths" of the biological tissue. Thus, when energy meter 620 indicates a 'maximum voltage' across thermocouple 605, this is indicative that apparatus 100 is operating at a "hot mode" driving frequency. This information about the driving frequency may be saved for later use.

When the apparatus 100 is in "cold mode," then the ultrasound energy is "deeper penetrating" and this is detected by receiving transducer 630 which is operatively linked to energy meter 610. Thus, when energy meter 610 indicates a 'maximum voltage' across receiving transducer 630, this is indicative that apparatus 100 is operating at a "cold mode" driving frequency. This information about the driving frequency may be saved for later use.

FIG. 23 is a flow chart of an exemplary frequency-tuning routine to "search" for a "best" operating frequency. In some embodiments, one or more steps of the routine of FIG. 23 are carried out automatically at least in part by controller 120.

In FIG. 23, the frequency tuning is used in order to locate a "hot mode" or "cold mode" resonance frequency of sonotrode 140.

In step S851, transducer 130 is operated at a plurality of "candidate frequencies." For each candidate frequency, a respective indication of a power of ultrasound waves produced by ultrasound transducer 130 is determined. It may be assumed that the candidate frequency associated with a "local maximum" of ultrasound wave power (i.e. local maximum with respect to frequency) is closest to the resonance frequency (i.e., hot mode or cold mode resonance frequency). Thus, in accordance with the power indications, an operating frequency of transducer 130 may then be selected.

In one example, the indication of the power of ultrasound waves produced by ultrasound transducer 130 may be a power consumption (or current consumption) of ultrasound transducer 130. In this example, a greater power consumption or current consumption of ultrasound transducer 130 may be indicative of a greater power of ultrasound waves produced by ultrasound transducer 130. In this example, apparatus 100 may include a meter (for example, a current meter) for measuring an indication of current consumption by ultrasound transducer 130.

In another example, one or more "measuring transducers" (NOT SHOWN) may be associated with sonotrode 140 to measure an intensity of ultrasound vibrations or waves propagating within sonotrode 140.

In step S855, the ultrasound transducer is operated at the selected "candidate frequency." As indicated in FIG. 23, steps s851 and S855 may be repeated a number of times (for example, at least about 5 times or at least about 10 times or at least about 20 times within a given time period—for example, within 2 minutes or within 1 minute or within 30 seconds or within 15 seconds). In one example, the resonant frequency (either for hot mode or cold mode) may "drift" or change over time, and thus, repeating steps S851 and S855 over time may be useful for periodically "re-tuning" apparatus 100.

In some embodiments, device controller 120 is configured to: i) effect a frequency scan by operating the ultrasound transducer 130 at a plurality of different candidate frequencies and determining, for each given candidate frequency of the plurality of frequencies, a respective indication of a power of ultrasound waves generated by the ultrasound transducer 130 that is associated with the given candidate frequency; ii) in accordance with the power indications, select an operating frequency from the plurality of candidate frequencies; and iii) operate the transducer 130 at the selected frequency for at least 10 seconds.

A Discussion of Power Consumption of Apparatus 100

There is no explicit limitation on the power consumption of apparatus 100.

In one non-limiting example, (i) electrical power consumed by whole system is up to 2 A*70 V=140-150 watts, and (ii) the efficiency of conversion of electrical power to acoustic power is 40-50% approximately. According to this non-limiting example, taking into account the efficiency of HF-power source 80-90%, then around 40-80 watts of acoustic power are provided. In this example, irradiative surface of sonotrode is ~6 cm$^2$ approximately. Therefore the energy flux from the acoustic irradiative surface is 7-13 watts/cm$^2$.

Applying Ultrasound Pulses

Figure 24:
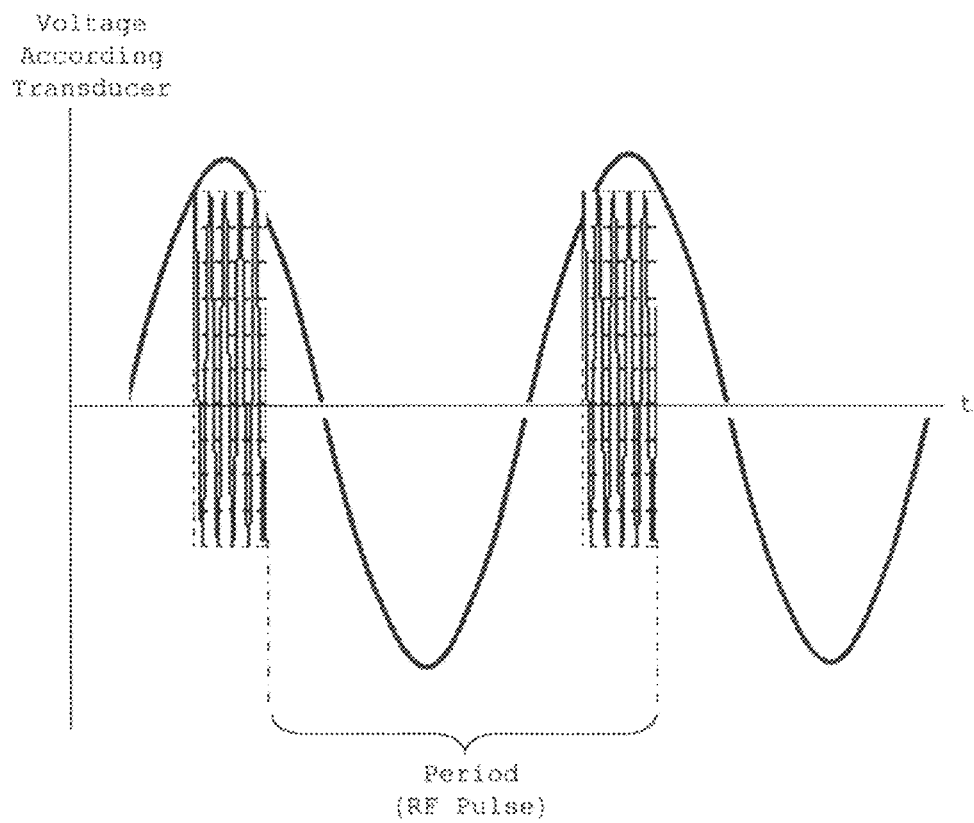
FIG. 24 illustrates the delivery of pulses of electrical current to an ultrasound transducer.

In some embodiments, apparatus 100 may operate in "hummer mode" where a plurality of pulses of ultrasound energy are delivered using sonotrode 140. In some embodiments, this may be carried by delivering a current pulses to transducer 130. Thus, in some embodiments, device controller 120, which regulates current provided to transducer 130, is configured as a pulse generator (or is operatively linked to a pulse generator), and may provide a current having a profile similar to the profile illustrated in FIG. 24.

Thus, in some embodiments, current (and hence ultrasound energy) is provided as a series of relatively "short" enforced ultrasonic pulses. This may be useful, for example, for drug delivery technology.

In some embodiments, the frequency of modulation can be between 1 Hz and 100 Hz.

In some embodiments, a ratio between a pulse width and the "distance between pulses" (i.e. in time units) is at most 0.5, or at most 0.3, or at most 0.1 or at most 0.05.

In some embodiments, a ratio between a peak power of transducer 130 and an average power of transducer 130 (for example, over a time period that is at least 1 second or 5 seconds or 10 seconds or 30 seconds) is at least 1.5, or at least 3, or at least 5, or at least 10.

Thus, in some embodiments, the pulse generator is operative to establish a value of said duty cycle parameter that is between 1% and 100%.

In some embodiments, the pulse generator is operative to establish a value of said duty cycle parameter that is between 15% and 30%.

In some embodiments, the pulse generator is operative to establish a rectangular pulse shape.

Thus, in some embodiments, a current source 110 provides electrical current to transducer 130, and device controller 120 is operative to cause the electromagnetic energy source to deliver said output electromagnetic signal as a pulsed signal having one or more pulse parameters, said pulse controller operative to effect a pulse-width modulation of the electrical current provided to transducer 130.

In some embodiments, at least one pulse parameter is selected from the group consisting of an amplitude, pulse duration, a pulse shape, a duty cycle parameter, a pulse sequence parameter, a pulse rise-time, and a pulse frequency.

A Discussion of FIGS. 25A-25B—Undulating Membrane Geometry

FIG. 25A-25B illustrates an example adipocyte which has been subjected to ultrasound waves in accordance with some embodiments of the present invention.

One feature of the adipocyte of FIGS. 25A-25B is that undulating membrane geometry has been introduced to the adipocyte.

In some embodiments, the ultrasound energy may do this on a relatively "large scale" and introduce undulating membrane geometry in at least 30% (or at least 10% or at least 50%) of the adipocytes within the control volume of FIG. 10.

In some embodiments, introduction of the undulating membrane geometry deformation increases membrane surface area by at least 20% without increasing adipocyte volume by more than 5%. (for example, see "Face 1" in FIG. 25B).

In some embodiments, introducing of the undulating membrane geometry increases, by at least 50%, a surface area of a contiguous cell membrane portion whose mass is 15% of a total cell membrane mass. Thus, as shown in FIG. 25B, the surface area of a "subportion" of the cell membrane (i.e. see Face 1) may increase by at least 50%.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

All references cited herein are incorporated by reference in their entirety. Citation of a reference does not constitute an admission that the reference is prior art.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

What is claimed is:

1. A device for treating adipose tissue located beneath a patient's skin, the device comprising:
    a) a sonotrode including a proximal portion, a distal portion, and an elongated neck portion connecting the proximal portion to the distal portion, the sonotrode being dimensioned such that:
        (i) a ratio between a dimension of the neck portion parallel to an elongate axis of the neck and a dimension of the neck portion perpendicular to the elongate axis of the neck is at least 1.5;
        (ii) a ratio between a dimension of the distal portion perpendicular the elongate axis of the neck and a dimension of the distal portion parallel to the elongate axis of the neck is at least 2;
        (iii) a ratio between a dimension of the proximal portion perpendicular to the elongate axis of the neck and the dimension of the neck portion perpendicular to the elongate axis of the neck is at least 2.5; and
        (iv) a ratio between the dimension of the distal portion perpendicular to the elongate axis of the neck and the dimension of the neck portion perpendicular to the elongate axis of the neck is at least 2; and
    b) an ultrasound transducer,
        wherein the ultrasound transducer is operatively coupled to the proximal portion of the sonotrode and induces ultrasound vibrations in the distal portion.

2. The device of claim 1 wherein the ultrasound transducer induces both transverse and longitudinal ultrasound vibrations in the distal portion.

3. The device of claim 1 wherein the ultrasound transducer and the sonotrode are configured to provide a transverse wave mode where at least 30%, by energy, of the induced ultrasound vibrations within the distal portion are transverse ultrasound vibrations in a direction that is substantially perpendicular to the neck axis within a tolerance of 20 degrees.

4. The device of claim 3 wherein the ultrasound transducer and the sonotrode are configured such that, when in the transverse wave mode, the ultrasound transducer induces mechanical vibrations in the proximal portion and/or in the neck portion that:
    i) are a direction that is substantially parallel within a tolerance of 20 degrees to the elongate neck axis; and
    ii) have a power level that is at least 70% a power level of the induced ultrasound vibrations within the distal portion.

5. The device of claim 3, wherein, for at least one bounding volume within the distal portion, the induced ultrasound vibrations cause motion in a plane that is perpendicular to the neck axis such that a ratio between:
    i) a momentum of matter within the distal portion associated with the motion in the perpendicular plane; and
    ii) a product of a mass within the bounding volume and a kinetic energy associated with the motion in the perpendicular plane,
is at most 0.2.

6. The device of claim 1 wherein the ultrasound transducer and the sonotrode are configured to provide a longitudinal wave mode wherein at least 30%, by energy, of the induced ultrasound vibrations within the distal portion are longitudinal ultrasound vibrations in a direction that is substantially parallel to the neck axis within a tolerance of 20 degrees.

7. The device of claim 6 wherein the ultrasound transducer and the sonotrode are configured to provide both the transverse wave mode and the longitudinal wave mode such that:
    i) when in the transverse wave mode, the ultrasound transducer operates at a first ultrasound driving frequency; and
    ii) when in the longitudinal wave mode, the ultrasound transducer operates at a second ultrasound driving frequency that is different from the first ultrasound driving frequency.

8. The device of claim 7 wherein a difference between the first and second driving frequencies is at least 3 kHz.

9. The device of claim 7 wherein a ratio between:
    i) difference between the first and second driving frequencies; and
    ii) a maximum of the first and second driving frequencies is at least 0.1.

10. The device of claim 6 wherein:
i) the sonotrode and the ultrasound transducer provide both the longitudinal and the transverse wave mode; and
ii) the device further comprises:
c) a device controller operative to cause the sonotrode and the ultrasound transducer to:
I) effect a preliminary phase having a duration $t_{HOT}$ that is at least 10 seconds and at most 30 seconds where the sonotrode and the ultrasound transducer provide the longitudinal wave mode; and
II) after the preliminary phase, effect a main phase having a duration $t_{COLD}$ that is at least twice the duration $t_{HOT}$ of the preliminary phase where the sonotrode and the ultrasound transducer provide the transverse wave mode.

11. The device of claim 10 wherein the controller is operative to effect at least one of the following operations:
i) repeat the preliminary and the main phases at least 10 times;
ii) commence the main phase within 15 seconds of a completion of the preliminary phase; and/or
iii) carry out the main and preliminary phases such that a ratio between the duration $t_{COLD}$ of the main phase and the duration $t_{HOT}$ of the preliminary phase is at most 5.

12. The device of claim 1 further comprising:
c) a device controller configured to:
i) effect a frequency scan by operating the ultrasound transducer at a plurality of different candidate frequencies and determining, for each given candidate frequency of the plurality of frequencies, a respective indication of a power of ultrasound waves generated by the ultrasound transducer that is associated with the given candidate frequency;
ii) in accordance with the power indications, select an operating frequency from the plurality of candidate frequencies; and
iii) operate the transducer at the selected frequency for at least 10 seconds.

13. The device of claim 1 further comprising:
c) a current source for providing electrical current to transducer; and
d) a device controller operative to cause
said electromagnetic energy source to deliver said output electromagnetic signal as a pulsed signal having one or more pulse parameters, said pulse controller operative to effect a pulse-width modulation of the electrical current provided to transducer.

14. The device of claim 1 wherein the ultrasound transducer and the sonotrode are configured to deliver an energy flux via an energy delivery surface of the distal portion that is at least 7 watts/cm^2.

15. The device of claim 1 wherein the ultrasound transducer and the sonotrode are configured so that an energy of the induced ultrasound vibrations within the distal portion is at least 40 watts and/or at most 80 watts.

16. The device of claim 1 wherein:
i) the sonotrode includes an energy delivery surface for delivering energy of the induced ultrasound vibrations to the patient's skin; and
ii) when the transducer is in operation, the energy flux is at most 30% of the maximum energy flux on the energy on the energy delivery surface at a point on the energy delivery surface where the elongate axis of the neck intersects the energy delivery surface.

17. The device of claim 1 wherein the transducer induces transverse ultrasound vibrations within the distal portion so as to cause an alternating pinching and pulling on at least a portion of a surface of the distal portion.

18. The device of claim 1 wherein:
i) the sonotrode includes a convex energy delivery surface for delivering energy of the induced ultrasound vibrations to the patient's skin, the energy delivery surface having an area A and a center C; and
ii) a distance between the center and a point of maximum energy flux on the energy delivery surface is at least 0.2 times a square root of the area A.

19. The device of claim 1 wherein the ultrasound transducer is attached to the proximal portion of the sonotrode.

20. The device of claim 1 wherein an acoustic impedance of a distal portion of sonotrode is at least 5 MRayls.

21. The device of claim 1 wherein the sonotrode is axisymmetric about the elongate neck axis.

22. The device of claim 1 wherein the dimension of the distal portion perpendicular to the elongate axis of the neck is less than one quarter a transverse wave mode wavelength of a material of which the sonotrode is constructed.

23. The device of claim 1 wherein a distal surface of the distal portion includes at least one of:
i) multiple discontinuous surfaces;
ii) a plurality of protrusions positioned on the distal surface;
iii) a plurality of indentations;
iv) a plurality of vertical ridges positioned on the distal surface; and
v) a plurality of concentric circular ridges positioned on the distal surface.

24. The device of claim 23 wherein:
i) the transducer and sonotrode are configured so that a plurality of ultrasound nodes and/or anti-nodes are produced; and
ii) a distance between adjacent ridges is an integral multiple and/or a reciprocal of an integral multiple of a distance between at least one of adjacent nodes and adjacent anti-nodes.

25. The device of claim 1 wherein:
i) the sonotrode includes an energy delivery surface for delivering energy of the induced ultrasound vibrations to the patient's skin
ii) the energy delivery surface has surface properties to cause scattering of energy of mechanical waves of an ultrasound frequency that are delivered from the distal surface as a result of the induced ultrasound vibrations in the distal portion.

26. The device of claim 1 wherein the sonotrode includes a convex energy delivery surface for delivering energy of the induced ultrasound vibrations to the patient's skin.

* * * * *